(12) United States Patent
Viola

(10) Patent No.: US 7,189,207 B2
(45) Date of Patent: *Mar. 13, 2007

(54) BIOPSY SYSTEM HAVING A SINGLE USE LOADING UNIT OPERABLE WITH A TROCAR DRIVER, A KNIFE DRIVER AND FIRING MODULE

(75) Inventor: Frank Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 425 days.

This patent is subject to a terminal disclaimer.

(21) Appl. No.: 10/444,301

(22) Filed: May 23, 2003

(65) Prior Publication Data

US 2003/0216667 A1  Nov. 20, 2003

Related U.S. Application Data

(63) Continuation of application No. 09/659,468, filed on Sep. 11, 2000, now Pat. No. 6,712,773.

(51) Int. Cl.
*A61B 5/05* (2006.01)
*A61B 5/00* (2006.01)
*A61B 13/00* (2006.01)
*A61B 17/32* (2006.01)

(52) U.S. Cl. .................. 600/564; 600/566; 600/568; 606/167

(58) Field of Classification Search ........ 600/564–568; 604/164.01; 606/167, 170
See application file for complete search history.

(56) References Cited

U.S. PATENT DOCUMENTS

| | | | |
|---|---|---|---|
| 737,293 A | 8/1903 | Summerfeldt | |
| 1,167,014 A | 1/1916 | O'Brien | |
| 1,255,330 A | 2/1918 | Morgan et al. | |
| 1,585,934 A | 5/1926 | Muir | |
| 1,663,761 A | 3/1928 | Johnson | |
| 1,867,624 A | 7/1932 | Hoffman | |
| 2,505,358 A | 4/1950 | Gusberg et al. | |
| 2,705,949 A | 4/1955 | Silverman | |

(Continued)

FOREIGN PATENT DOCUMENTS

| | | |
|---|---|---|
| DE | 935625 | 11/1955 |
| DE | 1 817 555 | 12/1968 |
| EP | 0 010 321 | 10/1979 |
| EP | 0 207 726 | 6/1986 |
| EP | 0 221 007 | 10/1986 |

(Continued)

OTHER PUBLICATIONS

Brochure—"ASAP Automatic Soft Tissue Biopsy System" (2 pages) (Published before filing date Nov. 19, 2001).

(Continued)

*Primary Examiner*—Max Hindenburg
*Assistant Examiner*—Michael Apanius

(57) ABSTRACT

A biopsy system for retrieving biopsy tissue samples from different regions of the body is disclosed. The biopsy system includes a single use loading unit having a trocar assembly and a knife assembly. A trocar driver is operably connected to the trocar assembly and is actuable to move a trocar between retracted and advanced positions. The trocar driver is disengaged from the trocar assembly prior to firing the trocar into a target tissue mass to reduce drag on the trocar during firing. A knife driver is operably connected to the knife assembly such that when actuated, a knife is both rotatably and axially advanced about the trocar.

7 Claims, 27 Drawing Sheets

U.S. PATENT DOCUMENTS

| | | |
|---|---|---|
| 2,729,210 A | 1/1956 | Spencer |
| 2,919,692 A | 1/1960 | Ackerman |
| 3,400,708 A | 9/1968 | Scheidt |
| 3,477,423 A | 11/1969 | Griffith |
| 3,561,429 A | 2/1971 | Jewett et al. |
| 3,590,808 A | 7/1971 | Muller |
| 3,606,878 A | 9/1971 | Kellog, Jr. |
| 3,732,858 A | 5/1973 | Banko |
| 3,734,099 A | 5/1973 | Bender et al. |
| 3,844,272 A | 10/1974 | Banko |
| 3,929,123 A | 12/1975 | Jamshidi |
| 3,989,033 A | 11/1976 | Halpern et al. |
| 3,995,619 A | 12/1976 | Glatzer |
| 4,099,518 A | 7/1978 | Baylis et al. |
| 4,200,106 A | 4/1980 | Douvas et al. |
| 4,203,444 A | 5/1980 | Bonnell et al. |
| 4,210,146 A | 7/1980 | Banko |
| 4,220,155 A | 9/1980 | Kimberling et al. |
| 4,243,048 A | 1/1981 | Griffin |
| 4,246,902 A | 1/1981 | Martinez |
| 4,274,414 A | 6/1981 | Johnson et al. |
| 4,282,884 A | 8/1981 | Boebel |
| 4,306,570 A | 12/1981 | Matthews |
| 4,314,560 A | 2/1982 | Helfgott et al. |
| 4,340,066 A | 7/1982 | Shah |
| 4,396,021 A | 8/1983 | Baumgartner |
| 4,403,617 A | 9/1983 | Tretinyak |
| 4,461,305 A | 7/1984 | Cibley |
| 4,513,745 A | 4/1985 | Amoils |
| 4,517,977 A | 5/1985 | Frost |
| 4,530,356 A | 7/1985 | Helfgott et al. |
| 4,577,629 A | 3/1986 | Martinez |
| 4,589,414 A | 5/1986 | Yoshida et al. |
| 4,598,710 A | 7/1986 | Kleinberg et al. |
| 4,600,014 A | 7/1986 | Beraha |
| 4,603,694 A | 8/1986 | Wheeler |
| 4,643,196 A | 2/1987 | Tanaka et al. |
| 4,644,951 A | 2/1987 | Bays |
| 4,651,752 A | 3/1987 | Fuerst |
| 4,651,753 A | 3/1987 | Lifton |
| 4,660,267 A | 4/1987 | Wheeler |
| 4,662,869 A | 5/1987 | Wright |
| 4,667,684 A | 5/1987 | Leigh |
| 4,669,496 A | 6/1987 | Kemp et al. |
| 4,674,502 A | 6/1987 | Imonti |
| 4,678,459 A | 7/1987 | Onik et al. |
| 4,681,123 A | 7/1987 | Valtchev |
| 4,685,458 A | 8/1987 | Leckrone |
| 4,696,298 A | 9/1987 | Higgins et al. |
| 4,699,154 A | 10/1987 | Lindgren |
| 4,702,260 A | 10/1987 | Wang |
| 4,702,261 A | 10/1987 | Cornell et al. |
| 4,708,147 A | 11/1987 | Haaga |
| 4,711,250 A | 12/1987 | Gilbaugh, Jr. et al. |
| 4,733,662 A | 3/1988 | DeSatnick et al. |
| 4,733,671 A | 3/1988 | Mehl |
| 4,735,215 A | 4/1988 | Goto et al. |
| 4,776,346 A | 10/1988 | Beraha et al. |
| 4,781,186 A | 11/1988 | Simpson et al. |
| 4,781,202 A | 11/1988 | Janese |
| 4,799,494 A | 1/1989 | Wang |
| 4,819,635 A | 4/1989 | Shapiro |
| 4,838,280 A | 6/1989 | Haaga |
| 4,844,088 A | 7/1989 | Kambin |
| 4,850,354 A | 7/1989 | McGurk-Burleson et al. |
| 4,850,373 A | 7/1989 | Zatloukal et al. |
| 4,874,375 A | 10/1989 | Ellison |
| 4,881,551 A | 11/1989 | Taylor |
| 4,893,635 A | 1/1990 | de Groot et al. |
| 4,907,599 A | 3/1990 | Taylor |
| 4,917,100 A | 4/1990 | Nottke |
| 4,919,146 A | 4/1990 | Rhinehart et al. |
| 4,924,878 A | 5/1990 | Nottke |
| 4,936,835 A | 6/1990 | Haaga |
| RE33,258 E | 7/1990 | Onik et al. |
| 4,940,061 A | 7/1990 | Terwilliger et al. |
| 4,944,308 A | 7/1990 | Akerfeldt |
| 4,950,265 A | 8/1990 | Taylor |
| 4,953,558 A | 9/1990 | Akerfeldt |
| 4,958,625 A | 9/1990 | Bates et al. |
| 4,976,269 A | 12/1990 | Mehl |
| 4,982,739 A | 1/1991 | Hemstreet et al. |
| 4,989,614 A | 2/1991 | Dejter, Jr. et al. |
| 4,991,592 A | 2/1991 | Christ |
| 4,991,600 A | 2/1991 | Taylor |
| 5,000,745 A | 3/1991 | Guest et al. |
| 5,002,553 A | 3/1991 | Shiber |
| RE33,569 E | 4/1991 | Gifford, III et al. |
| 5,005,585 A | 4/1991 | Mazza |
| 5,006,114 A | 4/1991 | Rogers et al. |
| 5,009,391 A | 4/1991 | Steigerwald |
| 5,009,659 A | 4/1991 | Hamlin et al. |
| 5,011,473 A | 4/1991 | Gatturna |
| 5,011,490 A | 4/1991 | Fischell et al. |
| 5,012,818 A | 5/1991 | Joishy |
| 5,014,717 A | 5/1991 | Lohrmann |
| 5,018,530 A | 5/1991 | Rank et al. |
| 5,019,036 A | 5/1991 | Stahl |
| 5,019,088 A | 5/1991 | Farr |
| 5,019,089 A | 5/1991 | Farr |
| 5,021,059 A | 6/1991 | Kensey et al. |
| 5,026,384 A | 6/1991 | Farr et al. |
| 5,027,827 A | 7/1991 | Cody et al. |
| 5,031,634 A | 7/1991 | Simon |
| 5,035,248 A | 7/1991 | Zinnecker |
| 5,036,860 A | 8/1991 | Leigh et al. |
| 5,040,715 A | 8/1991 | Green et al. |
| 5,041,129 A | 8/1991 | Hayhurst et al. |
| 5,047,008 A | 9/1991 | de Juan, Jr. et al. |
| 5,047,040 A | 9/1991 | Simpson et al. |
| 5,048,538 A | 9/1991 | Terwilliger et al. |
| 5,053,014 A | 10/1991 | Van Heugten |
| 5,053,044 A | 10/1991 | Mueller et al. |
| 5,056,529 A | 10/1991 | de Groot |
| 5,057,082 A | 10/1991 | Burchette, Jr. |
| 5,057,085 A | 10/1991 | Kopans |
| 5,059,197 A | 10/1991 | Urie et al. |
| 5,060,658 A | 10/1991 | Dejter, Jr. et al. |
| 5,061,281 A | 10/1991 | Mares et al. |
| 5,074,311 A | 12/1991 | Hasson |
| 5,074,841 A | 12/1991 | Ademovic et al. |
| 5,074,871 A | 12/1991 | Groshong |
| 5,078,142 A | 1/1992 | Siczek et al. |
| 5,078,723 A | 1/1992 | Dance et al. |
| 5,080,655 A | 1/1992 | Haaga |
| 5,085,659 A | 2/1992 | Rydell |
| 5,087,265 A | 2/1992 | Summers |
| 5,090,419 A | 2/1992 | Palestrant |
| 5,092,873 A | 3/1992 | Simpson et al. |
| 5,106,364 A | 4/1992 | Hayafuji et al. |
| 5,111,828 A | 5/1992 | Kornberg et al. |
| 5,121,751 A | 6/1992 | Panalletta |
| 5,125,413 A | 6/1992 | Baran |
| 5,127,419 A | 7/1992 | Kaldany |
| 5,133,359 A | 7/1992 | Kedem |
| 5,133,360 A | 7/1992 | Spears |
| 5,135,481 A | 8/1992 | Nemeh |
| RE34,056 E | 9/1992 | Lindgren et al. |
| 5,146,921 A | 9/1992 | Terwilliger et al. |
| 5,152,744 A | 10/1992 | Krause et al. |
| 5,156,160 A | 10/1992 | Bennett |
| 5,161,542 A | 11/1992 | Palestrant |
| 5,174,300 A | 12/1992 | Bales et al. |
| 5,176,628 A | 1/1993 | Charles et al. |

| Patent | Date | Inventor |
|---|---|---|
| 5,178,625 A | 1/1993 | Groshong |
| 5,183,052 A | 2/1993 | Terwilliger |
| 5,183,054 A | 2/1993 | Burkholder et al. |
| 5,188,118 A | 2/1993 | Terwilliger |
| 5,192,291 A | 3/1993 | Pannek, Jr. |
| 5,195,533 A | 3/1993 | Chin et al. |
| 5,195,988 A | 3/1993 | Haaga |
| 5,197,484 A | 3/1993 | Kornberg et al. |
| 5,199,441 A | 4/1993 | Hogle |
| 5,211,651 A | 5/1993 | Reger et al. |
| 5,213,110 A | 5/1993 | Kedem et al. |
| 5,217,458 A | 6/1993 | Parins |
| 5,217,479 A | 6/1993 | Shuler |
| 5,222,966 A | 6/1993 | Perkins et al. |
| 5,224,470 A | 7/1993 | Schnepp-Pesch et al. |
| 5,224,488 A | 7/1993 | Neuffer |
| 5,224,945 A | 7/1993 | Pannek, Jr. |
| 5,226,909 A | 7/1993 | Evans et al. |
| 5,226,910 A | 7/1993 | Kajiyama et al. |
| 5,234,000 A | 8/1993 | Hakky et al. |
| 5,234,994 A | 8/1993 | Shiraki et al. |
| 5,236,334 A | 8/1993 | Bennett |
| 5,242,460 A | 9/1993 | Klein et al. |
| 5,243,994 A | 9/1993 | Ranaletta |
| 5,249,582 A | 10/1993 | Taylor |
| 5,249,583 A | 10/1993 | Mallaby |
| 5,250,059 A | 10/1993 | Andreas et al. |
| 5,250,065 A | 10/1993 | Clement et al. |
| 5,251,641 A | 10/1993 | Xavier |
| 5,254,105 A | 10/1993 | Haaga |
| 5,269,793 A | 12/1993 | Simpson |
| 5,269,797 A | 12/1993 | Bonati et al. |
| 5,269,798 A | 12/1993 | Winkler |
| 5,273,051 A | 12/1993 | Wilk |
| 5,273,519 A | 12/1993 | Koros et al. |
| 5,275,609 A | 1/1994 | Pingleton et al. |
| 5,282,476 A | 2/1994 | Terwilliger |
| 5,282,484 A | 2/1994 | Reger |
| 5,284,156 A | 2/1994 | Schramm et al. |
| 5,285,795 A | 2/1994 | Ryan et al. |
| 5,286,253 A | 2/1994 | Fucci |
| 5,290,303 A | 3/1994 | Pingleton et al. |
| 5,292,310 A | 3/1994 | Yoon |
| 5,301,684 A | 4/1994 | Ogirala |
| 5,306,260 A | 4/1994 | Kanner |
| 5,312,425 A | 5/1994 | Evans et al. |
| 5,313,958 A | 5/1994 | Bauer |
| 5,316,013 A | 5/1994 | Striebel, II et al. |
| 5,320,110 A | 6/1994 | Wang |
| 5,324,300 A | 6/1994 | Elias et al. |
| 5,335,671 A | 8/1994 | Clement |
| 5,336,176 A | 8/1994 | Yoon |
| 5,353,804 A | 10/1994 | Kornberg et al. |
| 5,366,463 A | 11/1994 | Ryan |
| 5,366,464 A | 11/1994 | Belknap |
| 5,366,468 A | 11/1994 | Fucci et al. |
| 5,368,045 A | 11/1994 | Clement et al. |
| 5,392,790 A | 2/1995 | Kanner et al. |
| 5,394,887 A | 3/1995 | Haaga |
| 5,403,334 A | 4/1995 | Evans et al. |
| 5,409,013 A | 4/1995 | Clement |
| 5,415,182 A | 5/1995 | Chin et al. |
| 5,417,703 A | 5/1995 | Brown et al. |
| 5,419,774 A | 5/1995 | Willard et al. |
| 5,425,376 A | 6/1995 | Banys et al. |
| 5,437,630 A | 8/1995 | Daniel et al. |
| 5,439,474 A | 8/1995 | Li |
| 5,449,001 A | 9/1995 | Terwilliger |
| 5,456,689 A | 10/1995 | Kresch et al. |
| 5,458,112 A | 10/1995 | Weaver |
| 5,476,101 A | 12/1995 | Schramm et al. |
| 5,477,862 A | 12/1995 | Haaga |
| 5,492,130 A | 2/1996 | Chiou |
| 5,501,664 A | 3/1996 | Kaldany |
| 5,505,210 A | 4/1996 | Clement |
| 5,505,211 A | 4/1996 | Ohto et al. |
| 5,507,298 A | 4/1996 | Schramm et al. |
| 5,511,556 A | 4/1996 | DeSantis |
| 5,526,822 A | 6/1996 | Burbank et al. |
| 5,535,755 A | 7/1996 | Heske |
| 5,538,010 A | 7/1996 | Darr et al. |
| 5,546,957 A | 8/1996 | Heske |
| 5,551,442 A | 9/1996 | Kanner et al. |
| 5,560,373 A | 10/1996 | De Santis |
| 5,564,436 A | 10/1996 | Hakky et al. |
| 5,570,699 A | 11/1996 | Kass |
| 5,595,185 A | 1/1997 | Erlich |
| 5,617,874 A | 4/1997 | Baran |
| 5,649,547 A | 7/1997 | Ritchart et al. |
| 5,655,542 A | 8/1997 | Weilandt |
| 5,752,923 A | 5/1998 | Terwilliger |
| 5,769,086 A | 6/1998 | Ritchart et al. |
| 5,775,333 A | 7/1998 | Burbank et al. |
| 5,817,033 A | 10/1998 | DeSantis et al. |
| 5,830,153 A | 11/1998 | Kass |
| 5,842,999 A | 12/1998 | Pruitt et al. |
| 5,916,175 A | 6/1999 | Bauer |
| 5,928,164 A | 7/1999 | Burbank et al. |
| 5,944,673 A | 8/1999 | Gregoire et al. |
| 5,964,716 A | 10/1999 | Gregoire et al. |
| 5,980,469 A | 11/1999 | Burbank et al. |
| 5,980,545 A | 11/1999 | Pacala et al. |
| 5,989,197 A | 11/1999 | Avaltroni |
| 5,993,399 A | 11/1999 | Pruitt et al. |
| 6,007,497 A | 12/1999 | Huitema |
| 6,017,316 A | 1/2000 | Ritchart et al. |
| 6,018,676 A | 1/2000 | Davis et al. |
| 6,022,324 A | 2/2000 | Skinner |
| 6,027,458 A | 2/2000 | Janssens |
| 6,086,544 A | 7/2000 | Hibner et al. |
| 6,193,673 B1 * | 2/2001 | Viola et al. .................. 600/568 |
| 6,436,054 B1 * | 8/2002 | Viola et al. .................. 600/562 |
| 6,554,779 B2 * | 4/2003 | Viola et al. .................. 600/568 |
| 6,712,773 B1 * | 3/2004 | Viola .......................... 600/564 |

FOREIGN PATENT DOCUMENTS

| | | |
|---|---|---|
| EP | 0 238 461 | 2/1987 |
| EP | 0 378 692 | 7/1990 |
| EP | 0 442 851 | 8/1991 |
| EP | 0 536 888 | 4/1993 |
| EP | 0 919 190 A2 | 11/1998 |
| EP | 0 995 400 | 4/2000 |
| FR | 1161400 | 7/1956 |
| FR | 1267960 | 6/1960 |
| FR | 2332743 | 11/1975 |
| SU | 400319 | 2/1974 |
| SU | 520976 | 12/1974 |
| SU | 483978 | 12/1975 |
| SU | 707576 | 3/1976 |
| SU | 648219 | 2/1979 |
| SU | 1178422 | 4/1984 |
| SU | 1456115 | 2/1989 |
| SU | 1537233 | 1/1990 |
| SU | 1614800 | 12/1990 |
| WO | WO 83/03343 | 10/1983 |
| WO | WO 91/01112 | 7/1991 |
| WO | WO 92/00040 | 1/1992 |
| WO | WO 93/12707 | 7/1993 |
| WO | WO 95/25465 | 9/1995 |
| WO | WO 95/27441 | 10/1995 |
| WO | WO 96/24289 | 8/1996 |
| WO | WO 99/15079 | 4/1999 |

| | | |
|---|---|---|
| WO | WO 00/30546 | 6/2000 |

OTHER PUBLICATIONS

Brochure—"When It Comes to Core Samples, I Demand Accuracy and Consistency for All My Patients" (Published before filing date Nov. 19, 2001).

Brochure—Surgical Dynamics Nucleotome System, Automated Percutaneous Lumbar Discectomy 3 pgs. (Published before filing date Nov. 19, 2001).

Brochure—Introducing The Singular Technology for Multi-Core Microcalcification Sampling—5 pages (Published before filing date Nov. 19, 2001).

BIOPSYS: Mammotome Multi-Probe and Motorized Driver Instructions for Use; 3 pgs.; 1994 Article—"Stereotaxic Needle Core Biopsy of Breast Legions Using a Regular Mammographic Table With An Adaptable Stereotaxic Device" -by Judy S. Caines et al.:AJR163, Aug. 1994; pp. 317-321.

Article- "Stereotactic Breast Biopsy with a Biopsy Gun", by Steve H. Parker, M.D. et al.; reprinted from RADIOLOGY, vol. 176,No. 3, pps. 741-747; Sep. 1990.

Article—"Stereotactic Percutaneous Breast Core Biopsy Technical Adaption and Initial Experience" by Captain Jeffrey D. Lovin, M.D. et al.; Breast Dis 1990: 3:135-143.

Article—"Selective Use of Image-Guided Large-Core Needle Biopsy of the Breast: Accuracy and Cost Effectiveness" by Anthony J. Doyle et al., AJR:165; Aug. 1995; pp. 281-284.

Article—"Breat Biopsy: A Comparative Study of Stereotaxically Guided Core and Excisional Techniques" by John J. Gisvold et al.; AJR:162; Apr. 1994; pp. 815-820.

Article—"Stereotactic Core Needle Biopsy of Mammographic Breast Lesions As A Viable Alternative to Surgical Biopsy"; by Raouf A. Mikhail et al.; Annals of Surgical Oncology. 1(5):363:367, 1994.

* cited by examiner

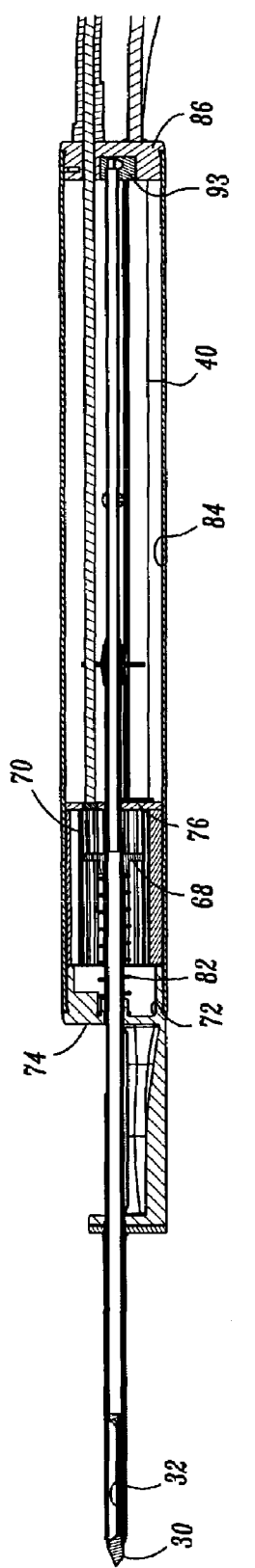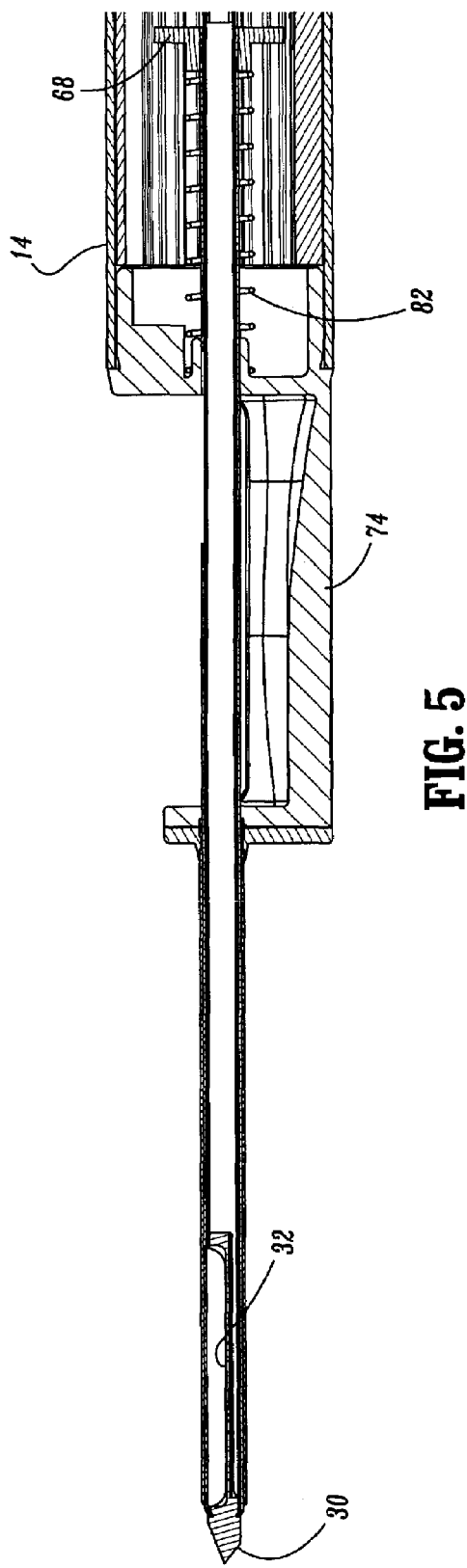
FIG. 4
FIG. 5

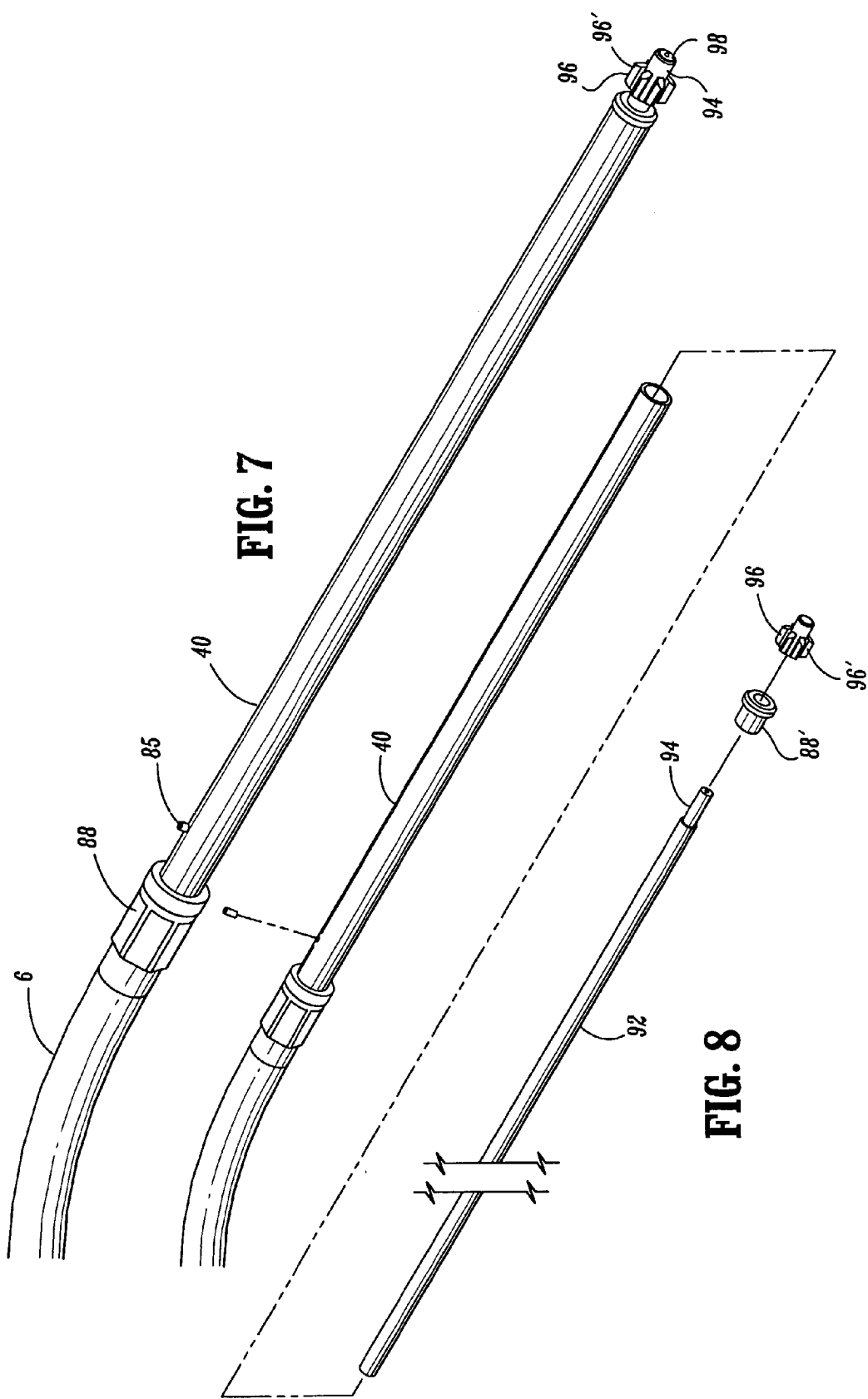

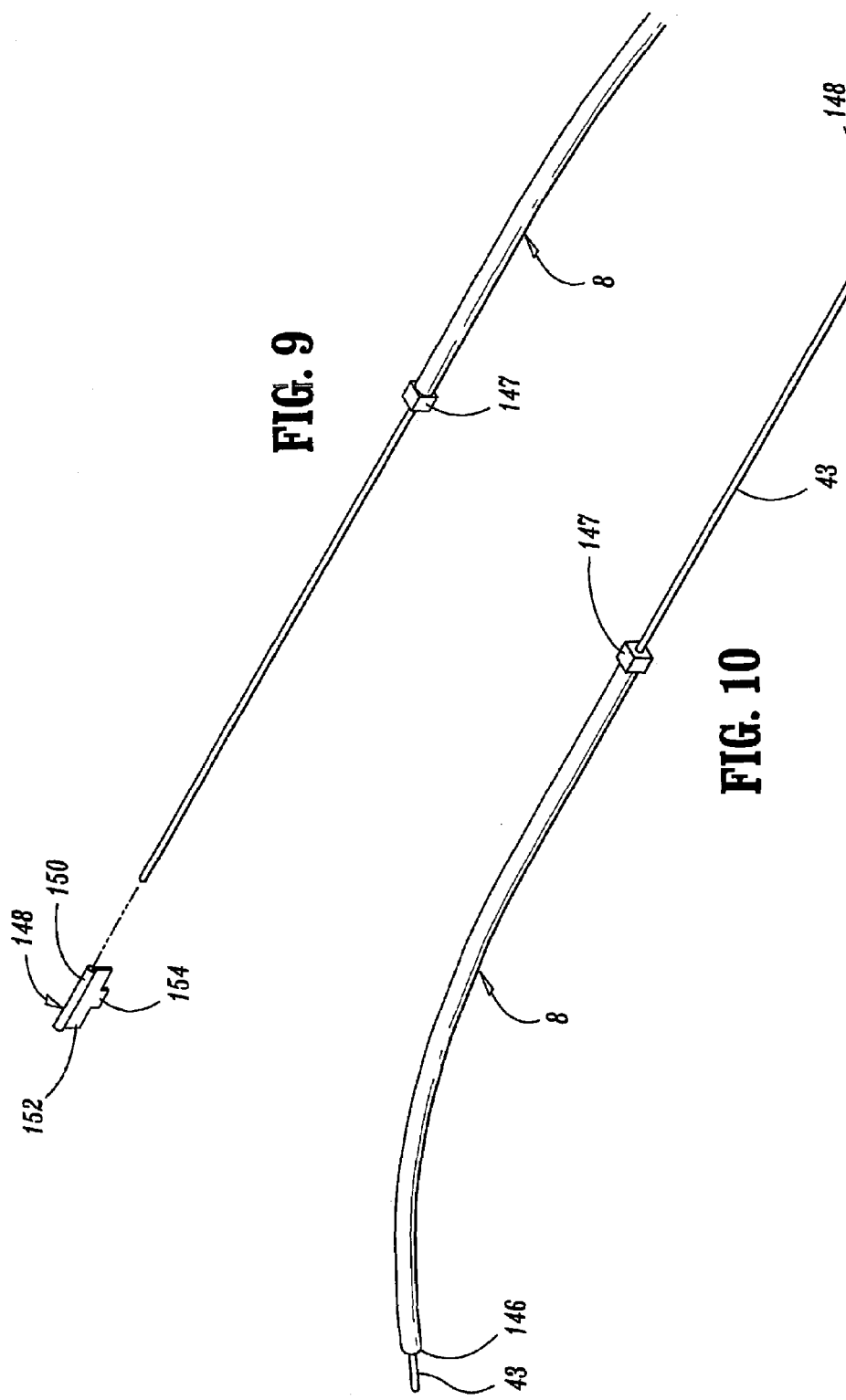

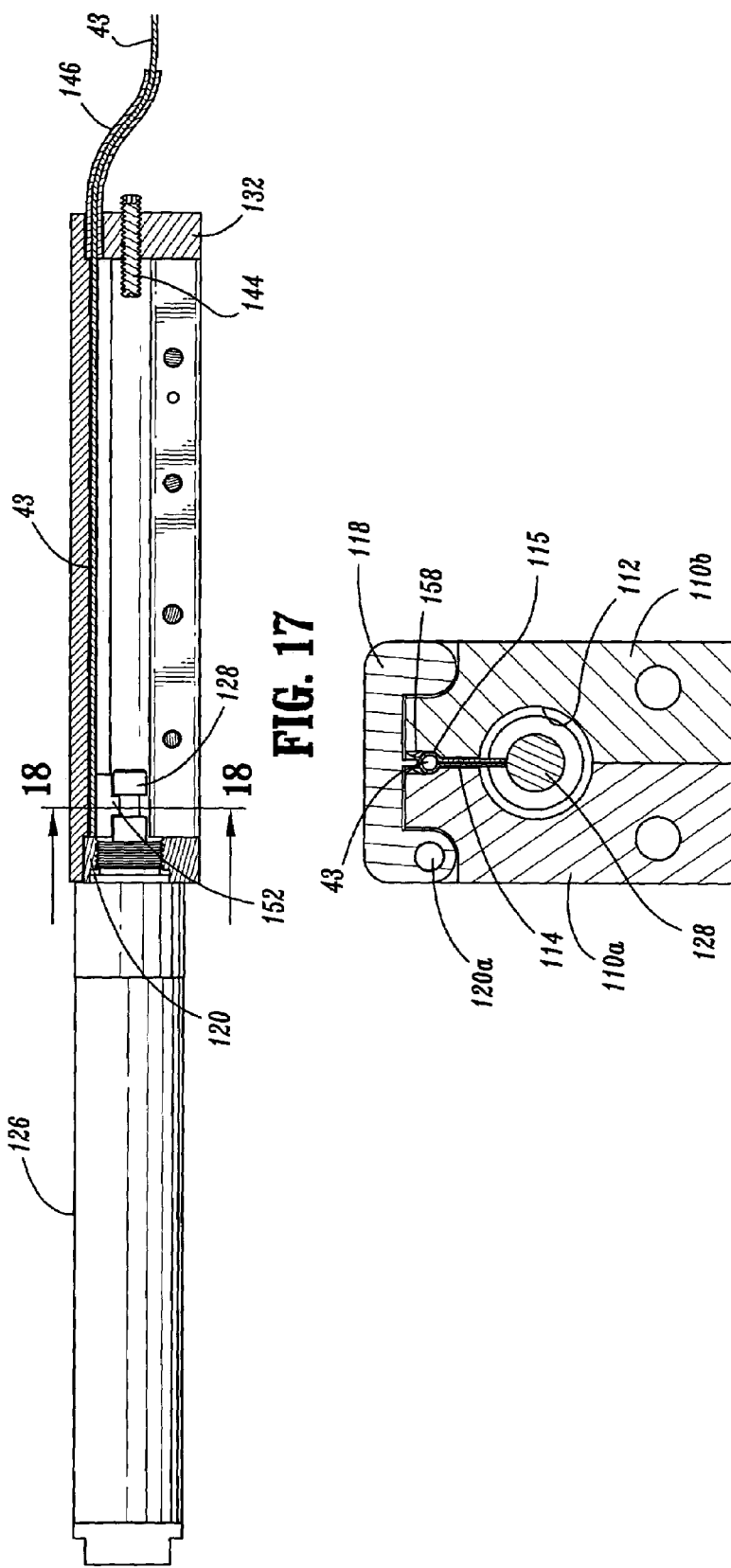
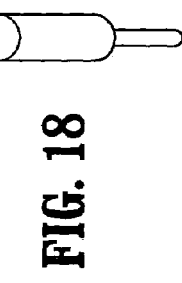
FIG. 17
FIG. 18

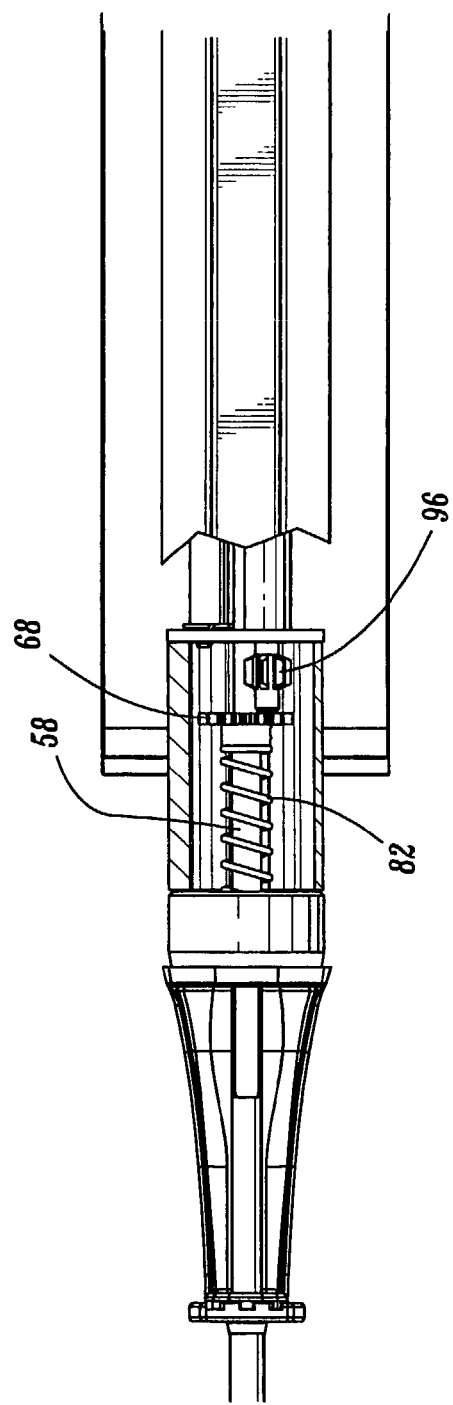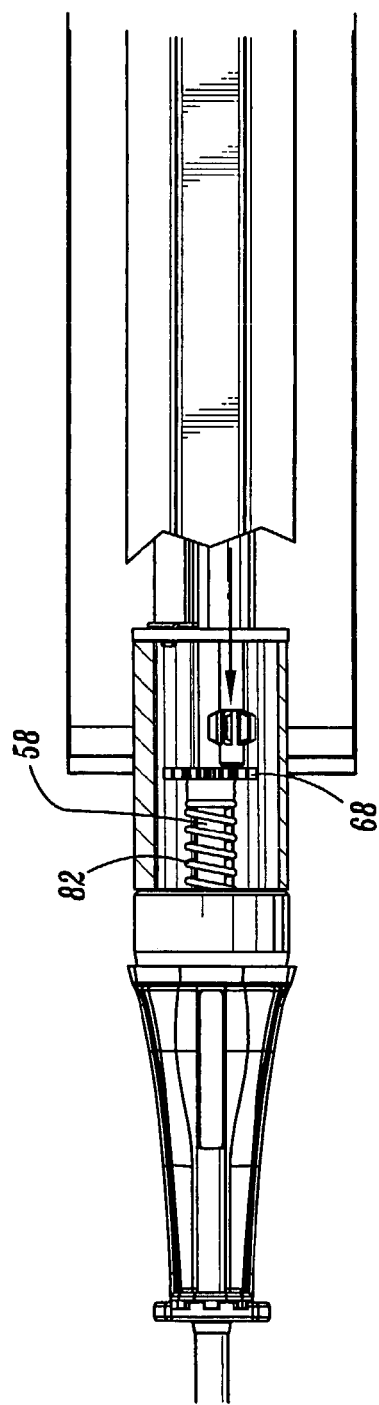

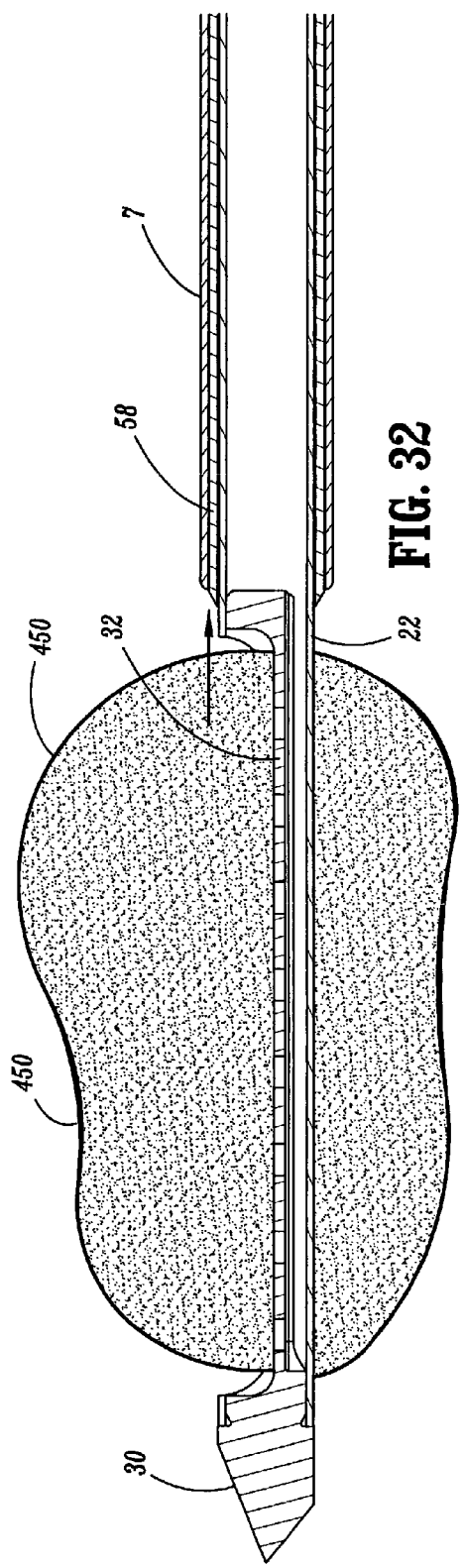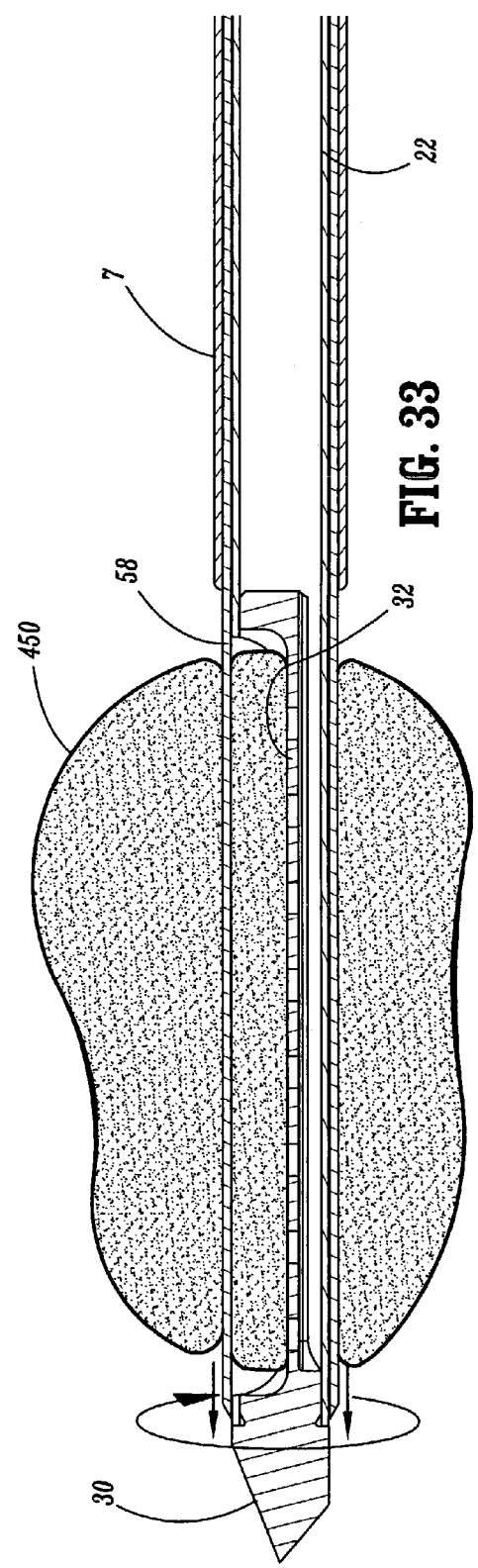

BIOPSY SYSTEM HAVING A SINGLE USE LOADING UNIT OPERABLE WITH A TROCAR DRIVER, A KNIFE DRIVER AND FIRING MODULE

CROSS REFERENCE TO RELATED APPLICATIONS

This application is a Continuation of U.S. patent application Ser. No. 09/659,468, filed on Sep. 11, 2000 now U.S. Pat. No. 6,712,773, the disclosure of which is hereby incorporated by reference herein.

BACKGROUND

1. Technical Field

This disclosure relates to an apparatus and method for the biopsy of tissue specimens and, more particularly, to a single insertion, multiple sample percutaneous biopsy system and method of use.

2. Background of Related Art

It is often necessary to sample tissue in order to diagnose and treat patients suspected of having cancerous tumors, pre-malignant conditions and other diseases or disorders. Typically, in the case of suspected cancerous tissue, when the physician establishes by means of procedures such as palpation, x-ray or ultrasound imaging that suspicious conditions exist, a biopsy is performed to determine whether the cells are cancerous. Biopsy may be done by an open or percutaneous technique. Open biopsy removes the entire mass (excisional biopsy) or a part of the mass (incisional biopsy). Percutaneous biopsy on the other hand is usually done with a trocar-like instrument and may be either a fine trocar aspiration (FNA) or a core biopsy. In FNA biopsy, individual cells or clusters of cells are obtained for cytologic examination and may be prepared such as in a Papanicolaou smear. In core biopsy, as the term suggests, a core or fragment tissue is obtained for histologic examination which may be done via frozen section or paraffin section. In more recent developments percutaneous techniques have been used to remove the entire mass during the initial procedure.

The type of biopsy utilized depends in large part on the circumstances present with respect to the patient and no single procedure is ideal for all cases. Core biopsy, however, is extremely useful in a number of conditions and is being used more frequently.

Intact tissue from the organ or lesion is preferred by medical personnel in order to arrive at a definitive diagnosis regarding the patient's condition. In most cases only part of the organ or lesion need be sampled. The portions of tissue extracted must be indicative of the organ or lesion as a whole. In the past, to obtain adequate tissue from organs or lesions within the body, surgery was performed so as to reliably locate, identify and remove the tissue. With present technology, medical imaging equipment such as stereotactic x-ray, fluoroscopy, computer tomography, ultrasound, nuclear medicine and magnetic resonance imaging, may be used. These technologies make it possible to identify small abnormalities even deep within the body. However, definitive tissue characterization still requires obtaining adequate tissue samples to characterize the histology of the organ or lesion.

Mammography can identify non-palpable (not perceptible by touch) breast abnormalities earlier than they can be diagnosed by physical examination. Most non-palpable breast abnormalities are benign but some are malignant. When breast cancer is diagnosed before it becomes palpable, breast cancer mortality can be reduced. It is still difficult to determine if pre-palpable breast abnormalities are malignant, as some benign lesions have mammographic features which mimic malignant lesions and some malignant lesions have mammographic features which mimic benign lesions. Thus, mammography has its limitations. To reach a definitive diagnosis, tissue from within the breast must be removed and examined under a microscope.

The introduction of stereotactic guided percutaneous breast biopsies offered alternatives to open surgical breast biopsy. With time, these guidance systems have become more accurate and easier to use. Biopsy guns were introduced for use in conjunction with these guidance systems. Accurate placement of the biopsy guns was important to obtain useful biopsy information because only one small core could be obtained per insertion at any one location. To sample the lesion thoroughly, many separate insertions of the instrument had to be made.

Biopsy procedures may benefit from larger tissue samples being taken, for example, tissue samples as large as 10 mm across. Many of the prior art devices required multiple punctures into the breast or organ in order to obtain the necessary samples. This practice is both tedious and time consuming.

One further solution to obtain a larger tissue sample is to utilize a device capable of taking multiple tissue samples with a single insertion of an instrument. An example of such a device is found in U.S. Pat. No. 5,195,533 to Chin et al. which describes a technique for extracting multiple samples with a single insertion of the biopsy device. Generally, such biopsy instruments extract a sample of tissue from a tissue mass by either drawing a tissue sample into a hollow trocar via an external vacuum source or by severing and containing a tissue sample within a notch formed on a stylet. Typical of such devices utilizing an external vacuum source are U.S. Pat. No. 5,246,011 issued to Cailouette and U.S. Pat. No. 5,183,052 issued to Terwiliger. Such devices generally contemplate advancing a hollow trocar into a tissue mass and applying a vacuum force to draw a sample into the trocar and hold the same therein while the tissue is extracted.

When extracting multiple samples with a single insertion of the biopsy device using suction to either draw in tissue or remove the tissue from the body, it is important that the vacuum path remain unclogged. If the vacuum path clogs, the sample removal will become difficult or impossible. This may necessitate multiple insertions of the device or reduce the sample mass per extraction.

Therefore, a continuing need exists for percutaneous biopsy apparatus and methods which can reliably extract adequate biopsy sample(s) with a single insertion of the biopsy instrument.

SUMMARY

In accordance with the present disclosure, a biopsy system is provided which includes a single use loading unit (SULU), a knife driver and a trocar driver. The SULU includes a trocar assembly having a tubular trocar defining a tissue receiving basket, a trocar tip having a basket insert fastened to the trocar, a trocar flange secured to the proximal end of the trocar, and an engagement mechanism for connecting the trocar driver to the trocar. The engagement mechanism includes a connecting member in the form of a notched flag. The connecting member is secured to one end of a drive shaft which extends between the trocar driver and the SULU. The notched flag is positioned to engage the trocar flange such that axial movement of the drive shaft effected by the trocar driver is translated to axial movement of the trocar. The connecting member is pivotable out of engagement with the trocar flange to disengage the trocar driver from the trocar to reduce drag on the system during firing of the trocar and enable advancement of the trocar into a target tissue mass at a higher velocity.

The knife assembly includes a tubular knife which is slidably positioned about the trocar. The knife has a sharpened distal edge and defines a tissue access window adjacent its proximal end. The knife is connected to knife driver through a flexible drive shaft and gear assembly such that the knife is both rotatably and axially driven by the knife driver.

BRIEF DESCRIPTION OF THE DRAWINGS

Various embodiments of the present disclosure are described herein with reference to the drawings, wherein:

FIG. 4 is a side cross-sectional view of the SULU shown in FIG. 2;

FIG. 5 is a side cross-sectional view of the forward end of the SULU shown in FIG. 2;

FIG. 7 is a perspective view of a portion of the knife assembly of the SULU shown in FIG. 2;

FIG. 8 is a perspective view with parts separated of the portion of the knife assembly shown in FIG. 7;

FIG. 9 is a perspective view with parts separated of the proximal end of the push/pull cable of the biopsy system shown in FIG. 1;

FIG. 10 is a perspective view of the proximal end of the push/pull cable of the biopsy system shown in FIG. 9;

FIG. 17 is a side cross-sectional view of the trocar driver shown in FIG. 15;

FIG. 18 is a cross-sectional view taken along section lines 18—18 of FIG. 17;

FIG. 30 is a side partial cross-sectional view of the central portion of the SULU with the knife assembly in the retracted position;

FIG. 31 is a side partial cross-sectional view of the central portion of the SULU with the knife assembly in a partially advanced position;

FIG. 32 is a side cross-sectional view of the distal end of the SULU disposed within a target tissue mass with the trocar assembly in the advanced position and the knife assembly in the retracted position and a vacuum drawing tissue into the basket;

FIG. 33 is a side cross-sectional view of the distal end of the SULU disposed within a target tissue mass with the trocar assembly and the knife assembly in the advanced positions and a severed tissue sample in the basket;

DETAILED DESCRIPTION OF PREFERRED EMBODIMENTS

Figure 1:
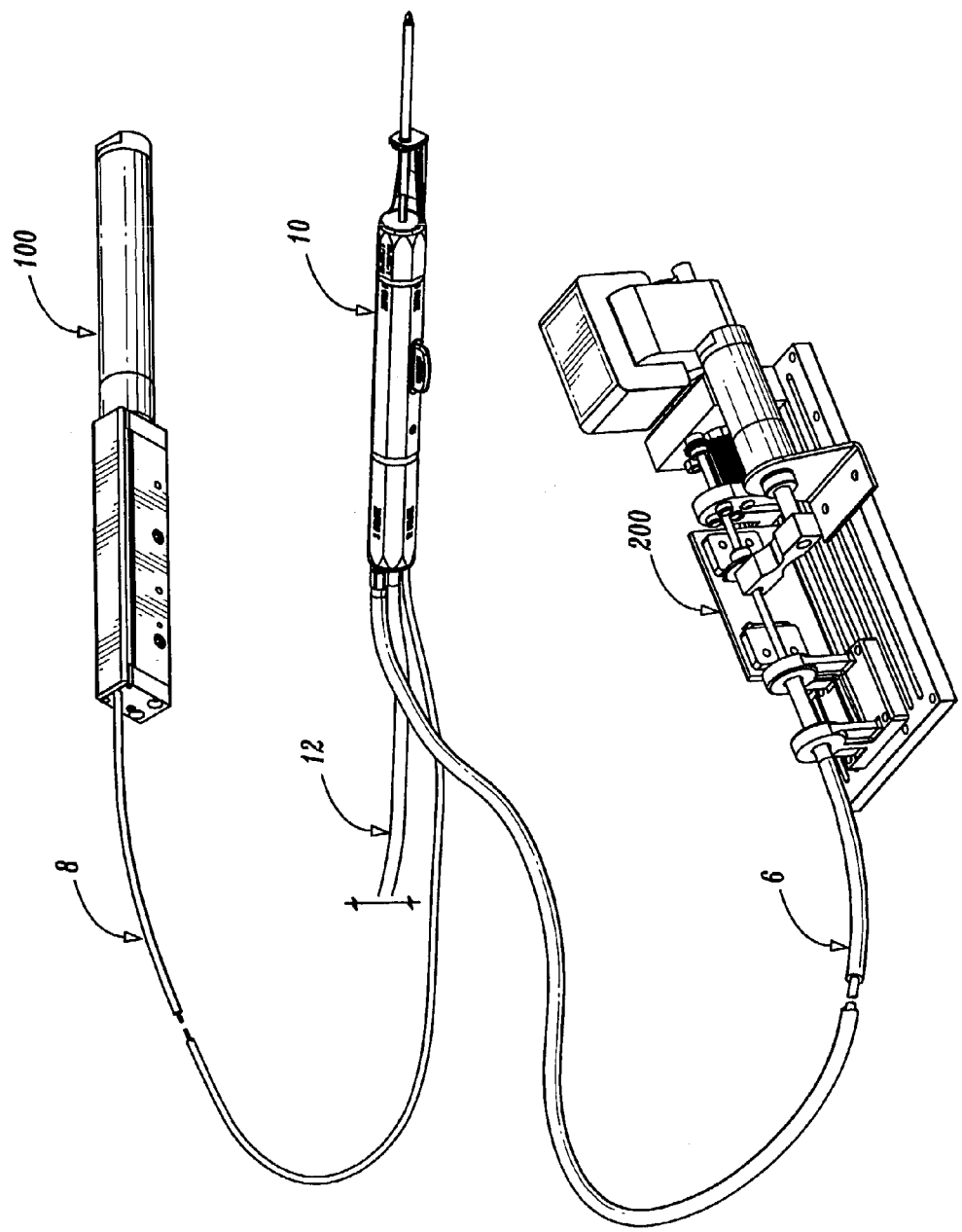
FIG. 1 is a perspective view of one embodiment of a biopsy system constructed in accordance with the principles of the present disclosure.

Preferred embodiments of the presently disclosed biopsy system will now be described in detail with reference to the drawings, wherein like reference numerals designate corresponding elements in each of the several views.

The following U.S. Patents and/or applications disclose related subject matter and are incorporated herein, in their entirety, by reference: U.S. Pat. No. 5,782,775, filed Jan. 14, 1996; U.S. Pat. No. 6,050,955, filed Sep. 18, 1998; U.S. Pat. No. 6,019,733, filed Sep. 18, 1998; U.S. Pat. No. 6,007,495, filed Jan. 22, 1998; U.S. patent application Ser. No. 09/252,548, filed Feb. 19, 1999 and U.S. patent application Ser. No. 09/448,238, filed Nov. 24, 1999.

The presently disclosed biopsy system is illustrated in FIG. 1 and includes a single use loading unit (SULU) 10, a trocar driver 100 and a knife driver 200. A knife driver cable 6 extends between knife driver 200 and SULU 10, and a push/pull cable 8 extends between trocar driver 100 and SULU 10. Trocar driver 100 and knife driver 200 will be described in further detail hereinbelow. A vacuum line 12 adapted to be connected to a vacuum source (not shown) is connected to SULU 10.

Figure 2:
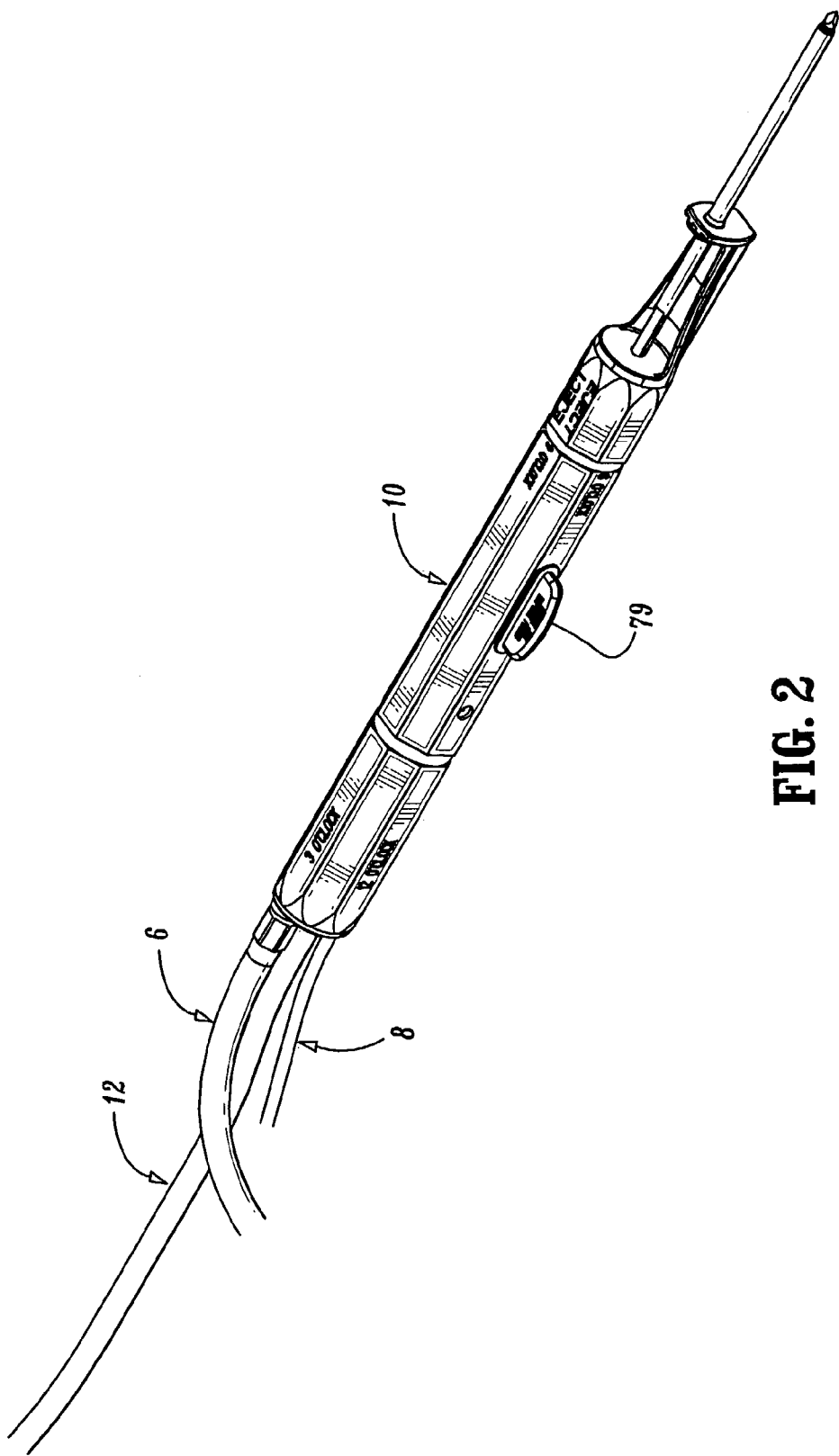
FIG. 2 is a perspective view of the single use loading unit ("SULU") of the biopsy system shown in FIG. 1.
Figures 3, 3A:
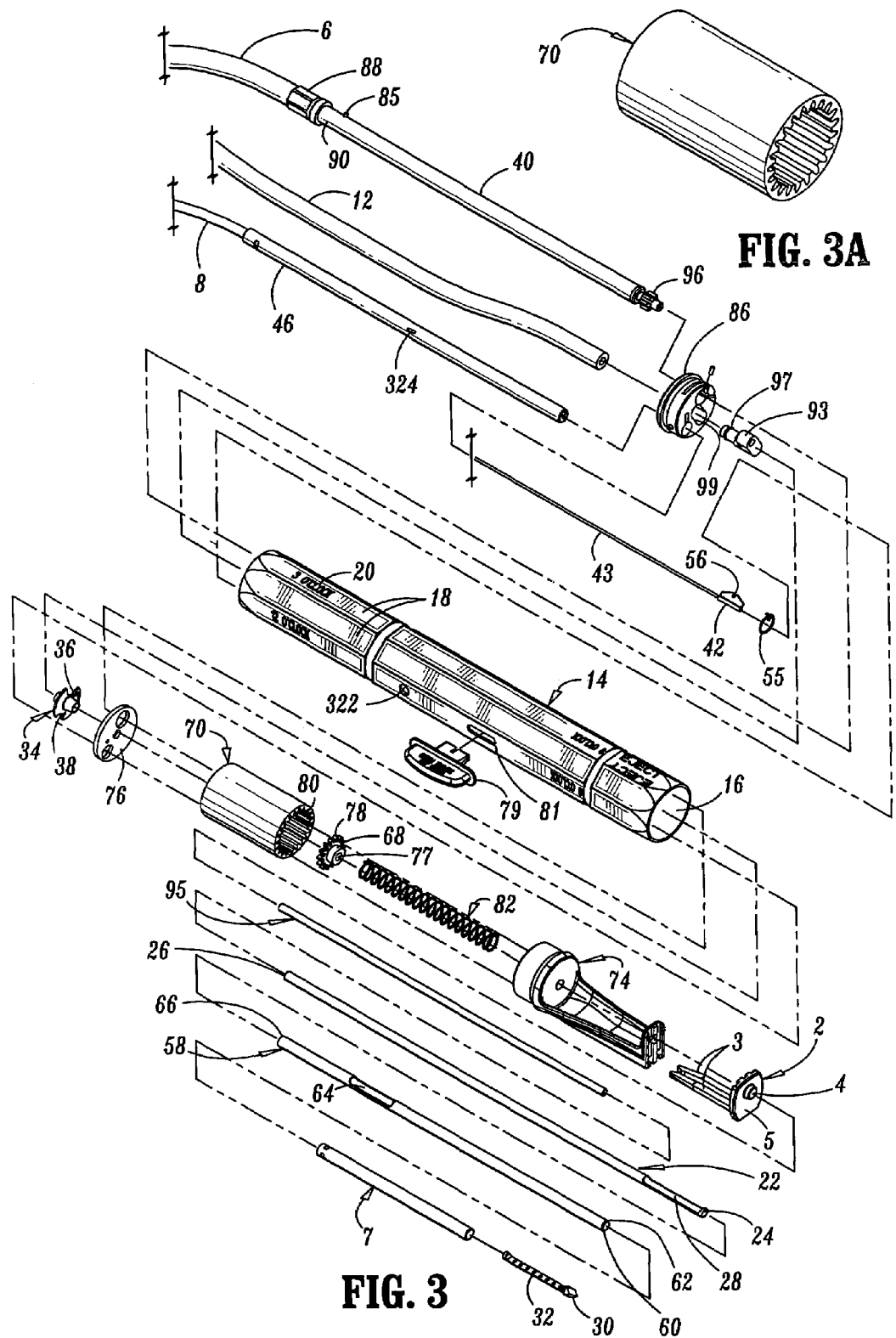
FIG. 3 is a perspective view with parts separated of the SULU shown in FIG. 2.
FIG. 3A is a perspective view of the internal gear of the SULU shown in FIG. 3.
Figure 6:
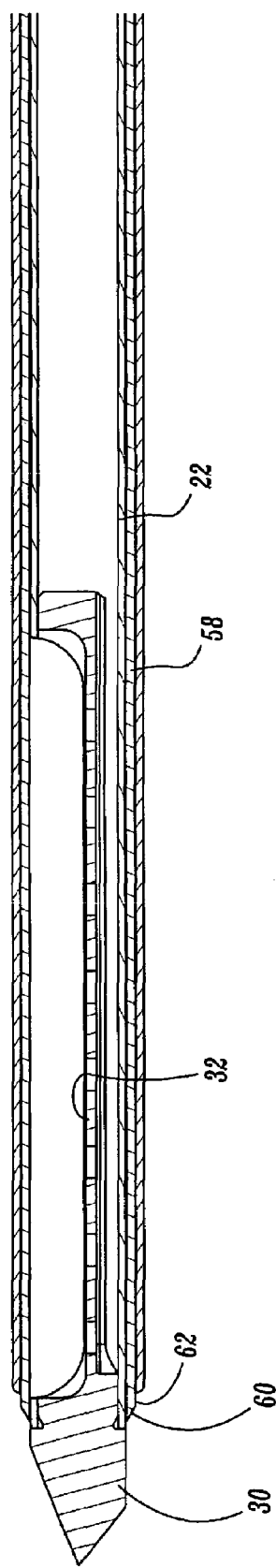
FIG. 6 is a side cross-sectional view of the distal end of the SULU shown in FIG. 2.

Referring to FIGS. 2 and 3, SULU 10 includes a trocar assembly and a knife assembly. The trocar assembly and the knife assembly are housed within tubular body 14 which defines a cylindrical throughbore 16. Tubular body 14 is preferably formed of aluminum but may be formed of any material having the requisite strength requirements including for example plastics. The outer surface of tubular body 14 is preferably hexagonal and defines a series of flats 18. Some or all of the flats may include indicia 20 to indicate the orientation of SULU 10. Two sets of indicia may be provided on each flat 18 to facilitate operation of SULU 10 from either side of the instrument. Alternately, the outer surface of SULU 10 can have a variety of configurations, e.g., cylindrical, pentagonal, square, etc.

Referring to FIGS. 3–6, the trocar assembly includes a tubular trocar 22 having a distal end 24 and a proximal end 26. Distal end 24 of trocar 22 includes a cutout which defines a tissue receiving basket 28. A trocar tip 30 having a perforated basket insert 32 is fastened to distal end 24 of trocar 22 such that basket insert 32 is positioned within tissue receiving basket 28 of trocar 22. Trocar tip 30 can be fastened within distal end of trocar 22 using any known fastening technique including crimping, adhesives, laser welding, etc.

Proximal end 26 of trocar 22 is fastened to a trocar flange 34 using any known fastening technique including, crimping, welding, adhesives, etc. Trocar flange 34 includes a pair of notches 36 and 38. Notch 36 is semi-spherically shaped and is dimensioned to slidably engage the outer surface of tubular member 40 see FIGS. 11 and 12. Tubular member 40 acts as a guide to maintain alignment of trocar flange 34 as it is moved through tubular body 14 by trocar driver 100 (FIG. 1). Tubular member 40 also forms part of the knife assembly and will be described in further detail below. Notch 38 of trocar flange 34 is configured to receive a flag 42. Flag 42 is preferably formed from a piece of folded sheet metal which is fastened to a first end of push/pull core 43 of push/pull cable 8. Alternately, flag 42 may be formed from other materials having the requisite strength requirements including plastic, etc. The second end of push/pull core 43 is secured within trocar driver 100 and will be described in further detail below. Flag 42 is preferably crimped to push/pull core 43 but other known fastening techniques may be used.

Figure 12:
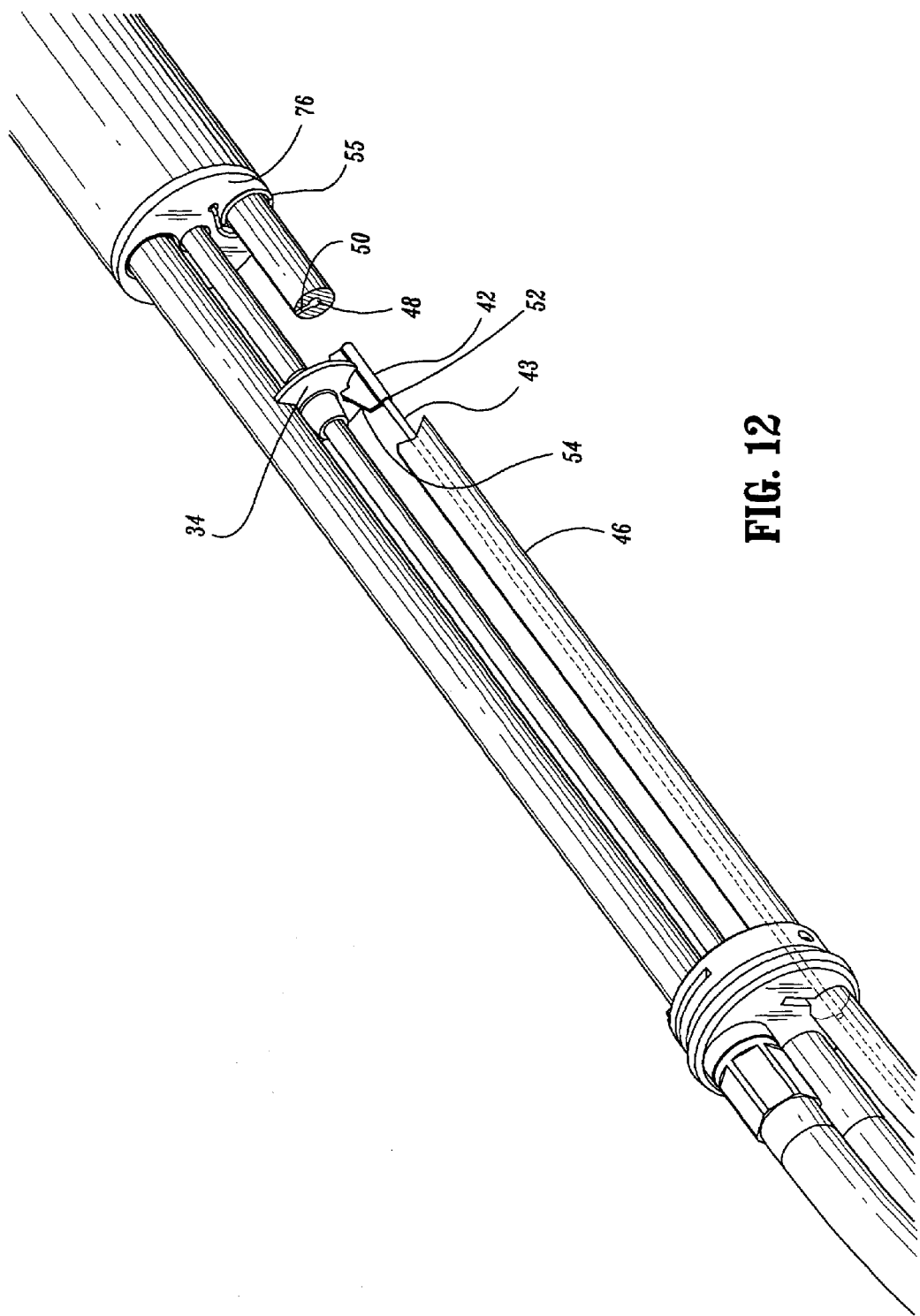
FIG. 12 is a perspective, partial cutaway view of the central portion of the SULU shown in FIG. 2 with the tubular body removed.

Referring also to FIG. 12, flag 42 is slidably positioned within a C-tube 46 which includes a central bore 48 and a radial slot 50. Hub 52 of flag 42 is fastened about push/pull core 43 and is slidably positioned within central bore 48 of C-tube 46. Central bore 48 of C-tube 46 is dimensioned to prevent buckling of push/pull core 43. Pennant portion 54 of flag 42 extends through radial slot 50 and includes a notch 56 which is positionable to engage trocar flange 34 adjacent notch 38. When flag 42 is positioned to engage trocar flange 34, any axial movement of driver shaft 43 is translated to axial movement of trocar flange 34, trocar 22 and trocar tip 30. C-tube 46 is rotatable to pivot pennant portion 54 and moves notch 56 from engagement with trocar flange 34 to disengage flag 42 from trocar flange 34. A spring 55 connected between a retainer 76 and C-tube 46 urges C-tube 46 to a position in which notch 56 is engaged with trocar flange 34. This will be discussed in further detail below.

Referring to FIGS. 3–8, the knife assembly includes a tubular knife 58 which is slidably positioned about trocar 22 and has an annular sharpened edge 60 formed at its distal end 62. A cutout formed towards proximal end 66 of knife 58 defines a tissue access window 64. A knife gear 68 is fastened to proximal end 66 of knife 58. Knife gear 68 is preferably molded about proximal end 66 of knife 58. Alternately, gear 68 can be fastened to proximal end 66 using any known fastening technique including welding, adhesives, crimping, etc. An internal gear 70 is positioned in a forward chamber 72 defined in tubular body 14 between a nosepiece 74 and a retainer 76. See FIG. 11. Nosepiece 74 and retainer 76 are fastened within throughbore 16 of tubular body 14 using any known fastening technique including welding, adhesives, etc. Knife gear 68 includes teeth 78 which engage teeth 80 formed on internal gear 70. A spring 82 is positioned about knife 58 between knife gear 68 and nosepiece 74. Spring 82 is positioned to urge knife gear 68 towards retainer 76 to urge knife 58 to a retracted position. Knife gear 68 includes a central throughbore 77 which is dimensioned to receive vacuum tube 95.

Figure 13:
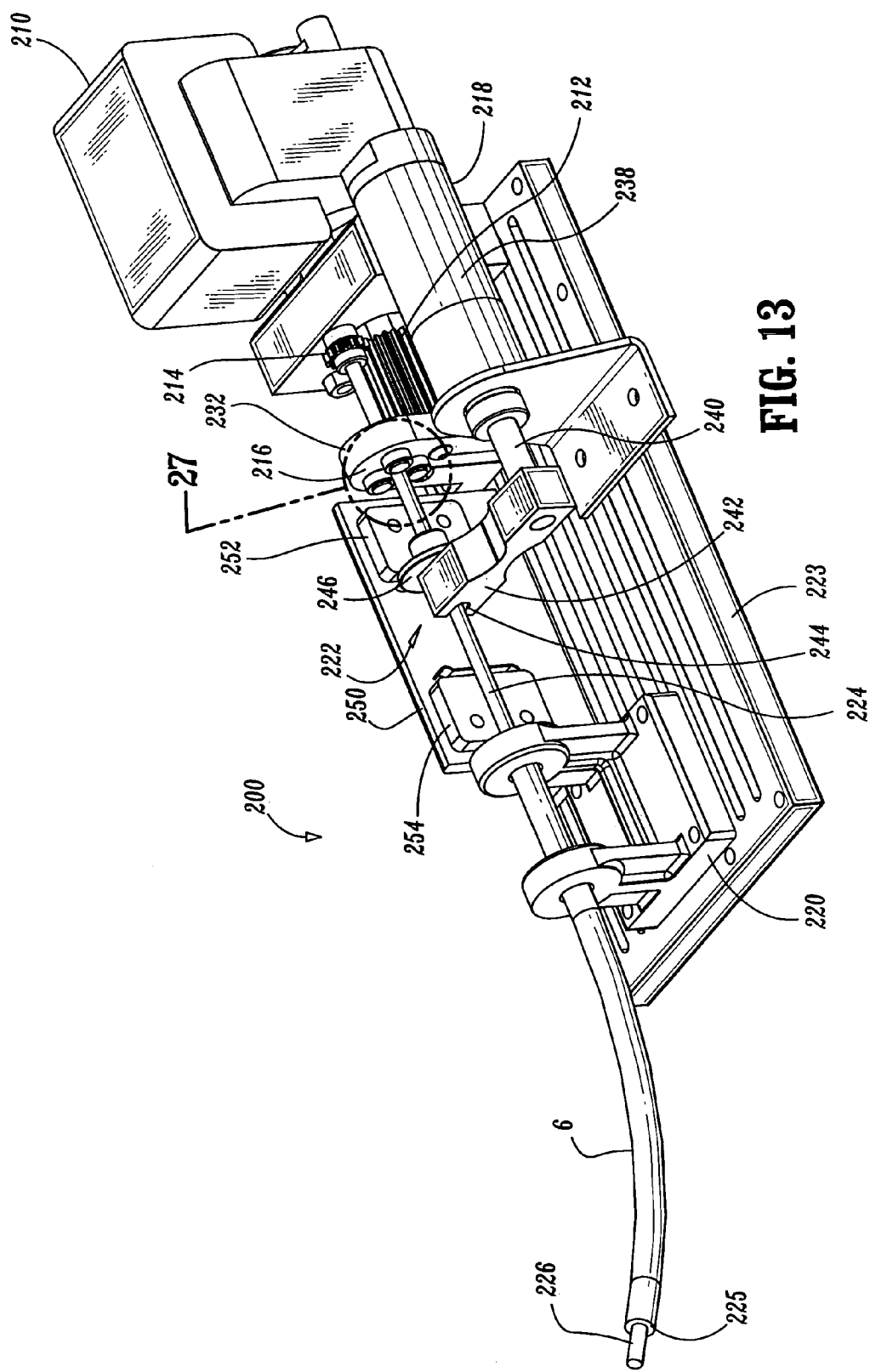
FIG. 13 is a perspective view of the knife driver of the biopsy system shown in FIG. 1.
Figure 14:
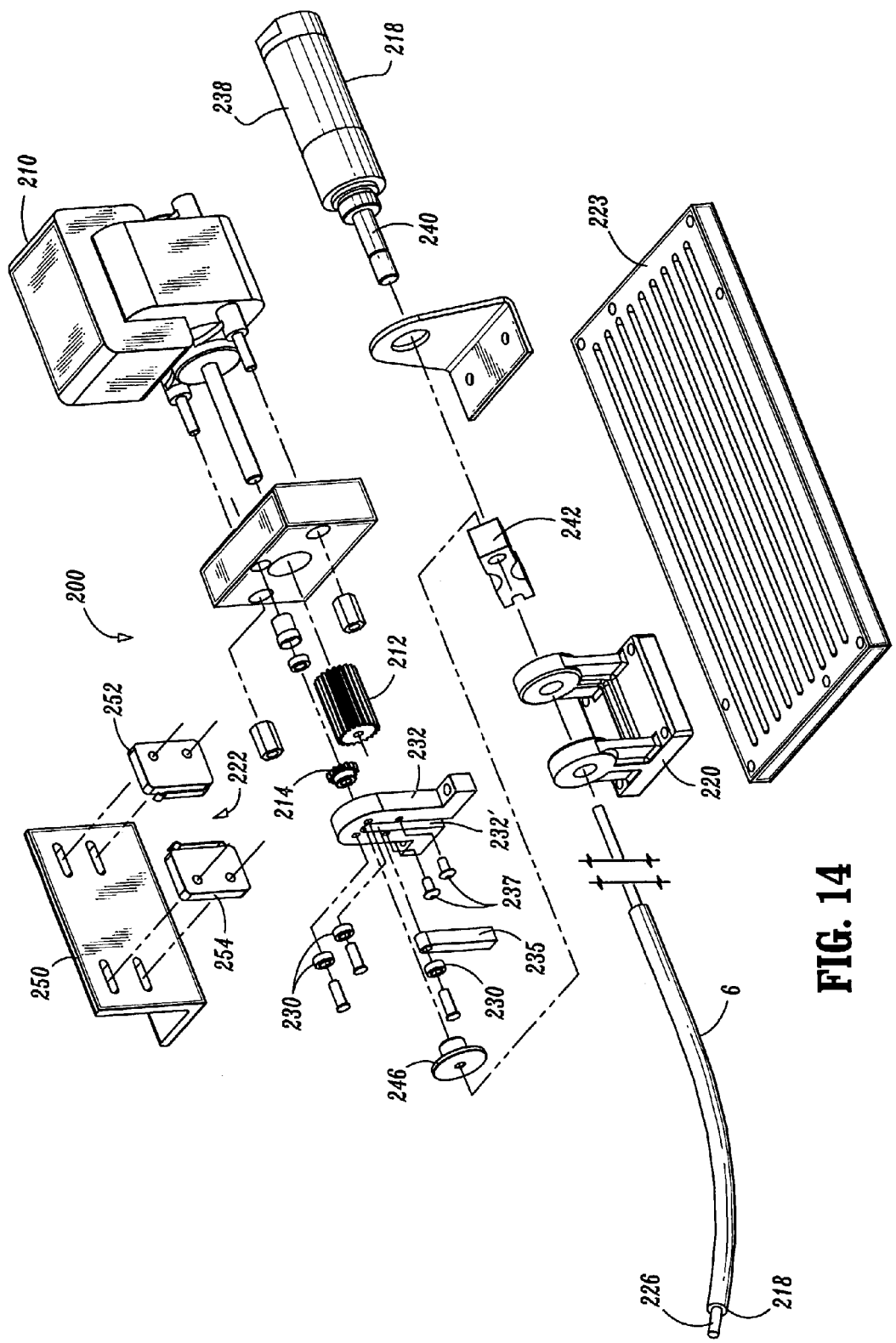
FIG. 14 is a perspective view with parts separated of the knife driver shown in FIG. 13.
Figure 15:
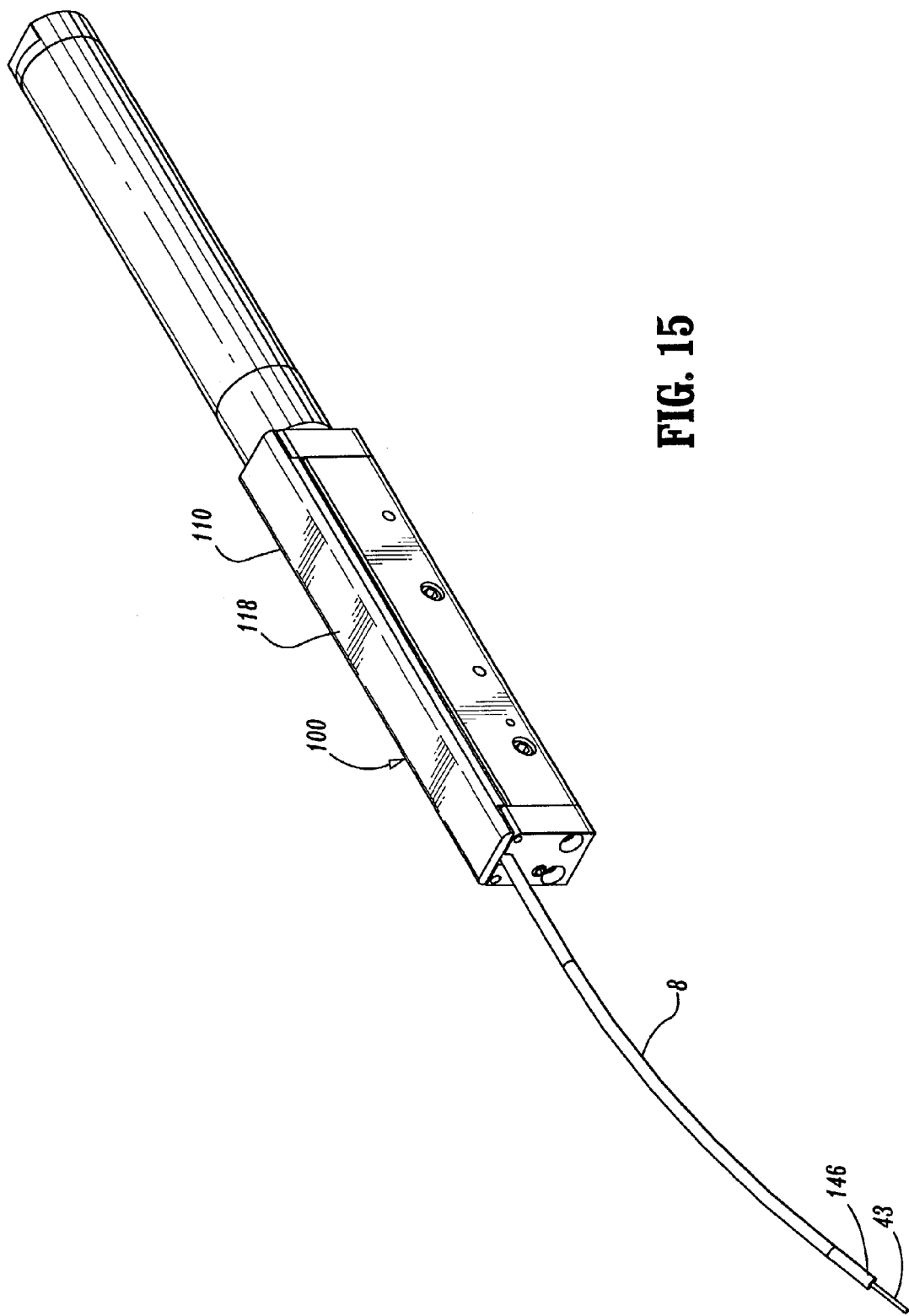
FIG. 15 is a perspective view of the trocar driver of the biopsy system shown in FIG. 1.
Figure 16:
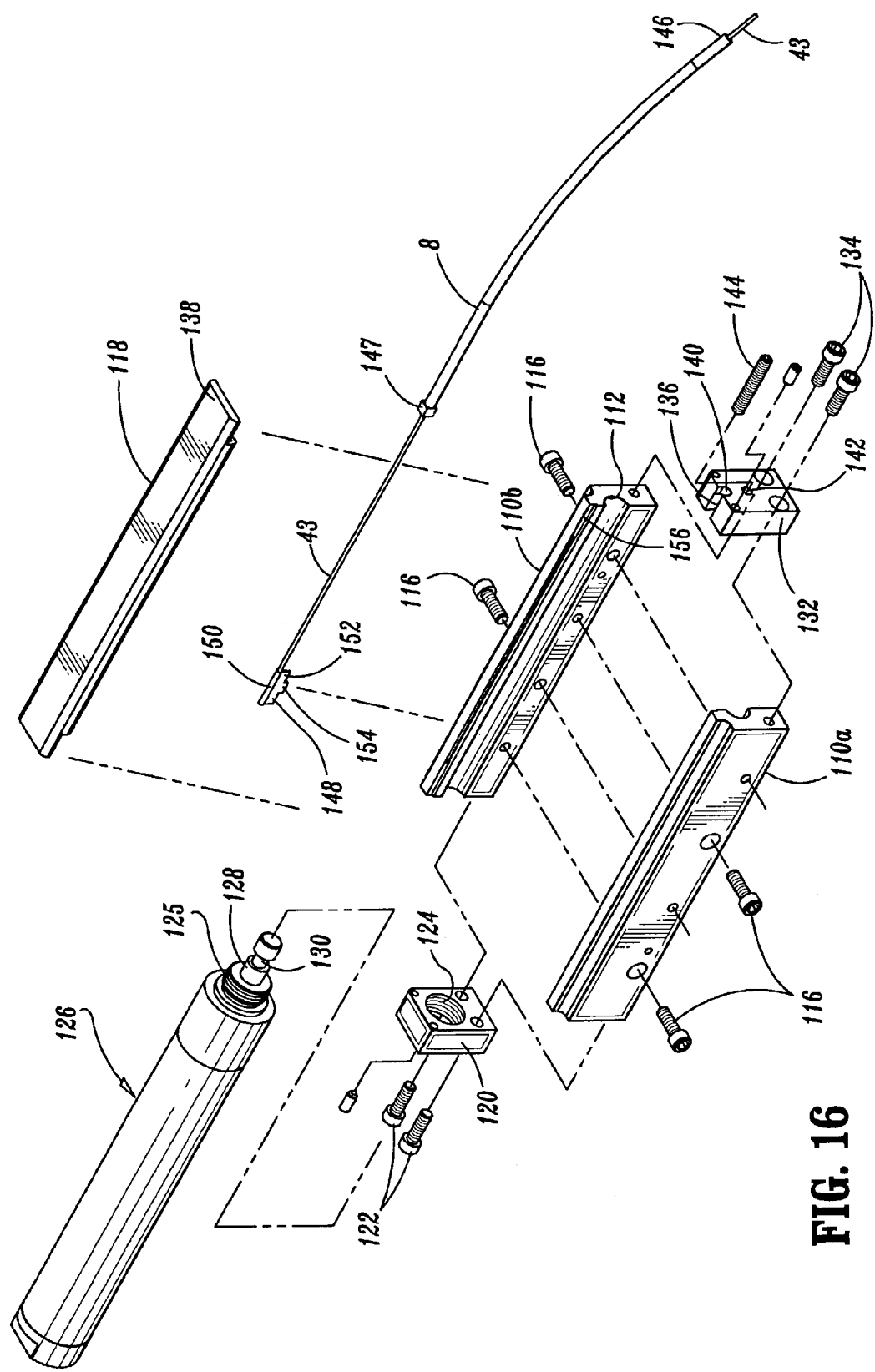
FIG. 16 is a perspective view with parts separated of the trocar driver shown in FIG. 15.

Tubular member 40 is positioned within a rear chamber 84 defined within tubular body 14 of SULU 10 between retainer 76 and an end cap 86. A pin 85 projects outwardly from tubular member 40. Pin 85 is received within an internal slot formed in end cap 86 to form a bayonet-type coupling therewith. See FIG. 11. A connector 88 is provided on a proximal end 90 of tubular member 40 to facilitate connecting tubular member 40 to an outer sheath 225 (FIG. 13) of knife driver cable 6. A bearing member 88' is secured to the distal of tubular member 40. A solid straight shaft 92 extends through tubular member 40 and includes a reduced diameter end portion 94 which extends through an opening in bearing member 88'. One end of shaft 92 is fastened to inner flexible shaft 226 of knife driver cable 6 (FIG. 13). A drive gear 96 is fastened to reduced diameter end portion 94 of shaft 92. Drive gear 96 can be fastened to shaft 92 using any known fastening technique including welding, crimping, brazing, etc. Drive gear 96 includes gear teeth 96'. A spherical nose 98 of end portion 94 extends axially from drive gear 96. Gear teeth 96' mesh with internal gear teeth 80 of internal gear 70 such that upon rotation of drive gear 96 by knife driver 200, internal gear 70 is rotated. Rotation of internal gear 70 causes knife gear 68 to rotate to provide corresponding rotation of knife 58. Spherical nose 98 of reduced diameter end portion 94 is positioned to engage the rear end of knife gear 68 such that when inner flexible shaft 226 of knife driver cable 6 is advanced by knife driver 200, spherical nose 98 of shaft 92 urges knife gear 68 axially along a path defined by internal gear teeth 80 to advance knife 58 axially. See FIG. 31. When drive gear 96 is retracted by knife driver 200, spring 82 returns knife gear 68 to its retracted position adjacent retainer 76.

Referring again to FIG. 3, a vacuum tube 95 extends into trocar 22. Vacuum tube 95 may include an outer seal (not shown) to seal between the internal surface of trocar 22 and the outer surface of vacuum tube 95. The proximal end of vacuum tube 95 is connected to an offset fitting 93 which is received in a bore 99 formed in end cap 86. Offset fitting 93 includes a plug 97 adapted to be sealingly received within one end of a vacuum line 12. Vacuum tube 95 is positioned to facilitate creation of a vacuum within trocar 22 to draw tissue into tissue receiving basket 28 of trocar 22.

A slide 2 including a pair of flexible legs 3 is adjustably mounted to nosepiece 74. Each leg 3 is resilient and includes a detent which is positionable in one of multiple grooves (not shown) formed in nosepiece 74. A bore 4 is formed in a base portion 5 of slide 2. Bore 4 is dimensioned to receive a tube 7 formed of a radiotranslucent material. Tube 7 is positioned about the distal end of knife 58 and trocar 22. Slide 2 is adjustable with respect to nosepiece 74 to selectively cover a portion of basket 28. Such is necessary when the length of basket 28 exceeds the width of the target tissue mass.

Figure 11:
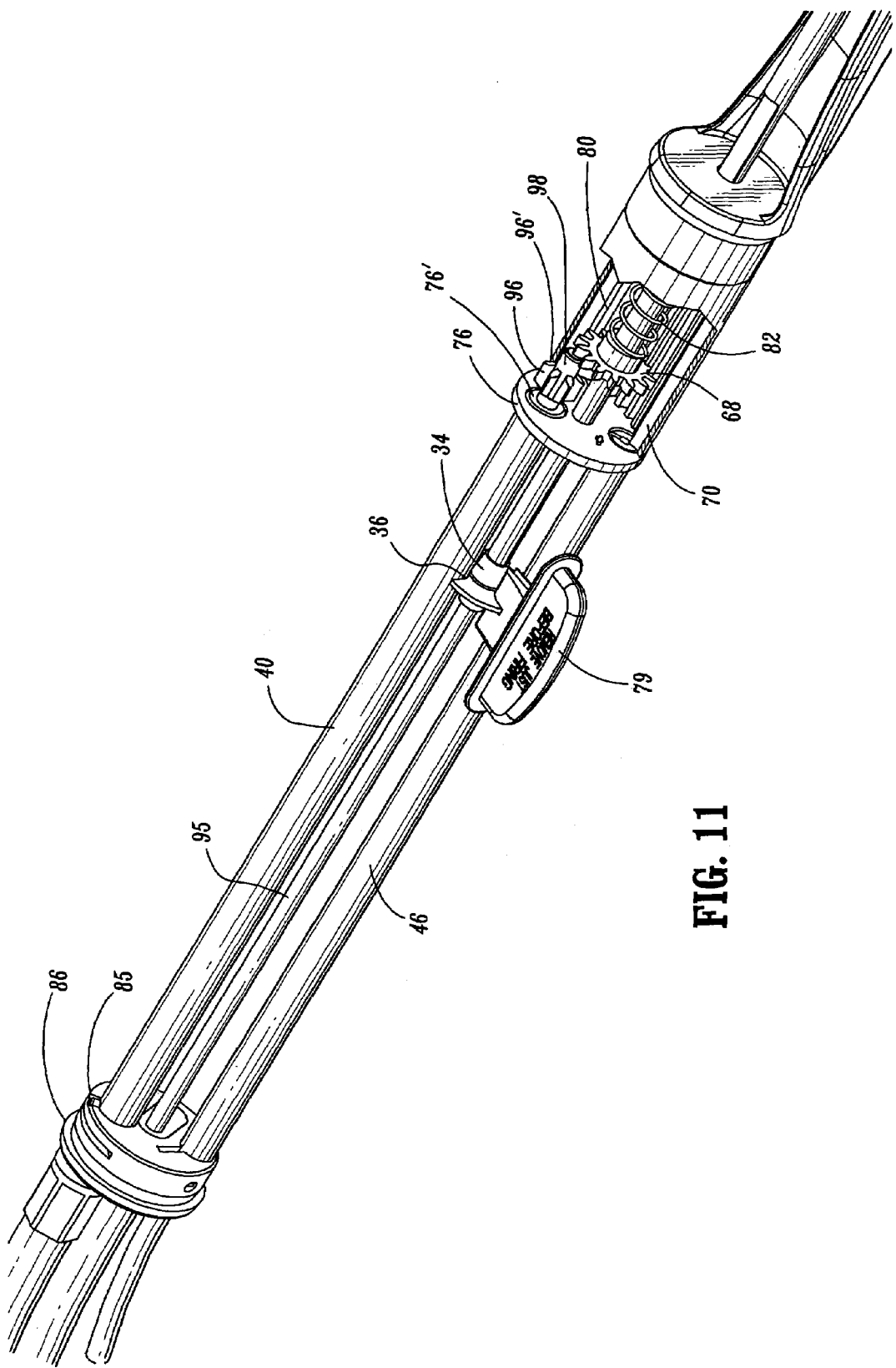
FIG. 11 is a perspective view of the central portion of the SULU shown in FIG. 2 with the tubular body removed.

Referring to FIGS. 11 and 12, as discussed above, a retainer 76 and an end cap 86 define a rear chamber 84 within tubular body 14. Retainer 76 and end cap 86 include openings which define bearing surfaces for supporting C-tube 46, vacuum tube 95 and tubular member 40. A shipping tab 79 extends through opening 81 (FIG. 3) in tubular body 14 into rear chamber 84 and engages trocar flange 34 to prevent axial movement of trocar 22 during shipping and/or during attachment of SULU 10 to trocar driver 100.

Preferably, SULU 10, excluding tubular member 40, solid shaft 94 and drive gear 96, is disposable after use. Cable 8 including push/pull core 43 may also be disposable. Tubular member 40, shaft 92 and drive gear 96 can be removed from SULU 10 by rotating connector 88 and tubular member 40 approximately 90° to disengage bayonet pin 85 from end cap 86 and, thereafter, pulling tubular member 40 and drive gear 96 through the opening 76' (FIG. 11) formed in retainer 76. Preferably, the disposable components of SULU 10 are constructed from engineering grade plastics, e.g., polycarbonates, nylon, delrin or like materials. The non-disposable elements, e.g., drive gear 96, may be formed of metal, e.g., stainless steel or other reusable materials having the requisite strength requirements.

Referring to FIGS. 15–18, trocar driver 100 includes a housing 110 formed of a pair of symmetrical housing halves 110a and 110b which define a cylindrical throughbore 112, extending slot 114 extending between throughbore 112 and cylindrical recess 115. Housing halves 110a and 110b are preferably secured together with screws 116, although other fastening techniques may be used to secure the housing halves together. A pivotable lid 118 is pivotably secured about rod 120a (FIG. 18) to housing half 110a. Lid 118 is pivotable to permit access to slot 114 during loading of push/pull core 43 into needle driver 100.

A first mounting block 120 is secured to one end of housing 110 using screws 122 or other known fastening techniques. Mounting block 120 includes a threaded throughbore 124 configured to threadably receive a threaded end 125 of drive cylinder 126. Drive cylinder 126 includes a drive member 128 which is configured to be slidably positioned within cylindrical throughbore 112. Drive member 128 includes an annular recess 130. A second mounting block 132 is secured to the end of housing 110 opposite mounting block 120 using screws 134. Second mounting block 132 includes a U-shaped slot 136. Lid 118 includes an extension 138 which covers U-shaped slot 136 when lid 118 is in a closed position. U-shaped slot 136 is dimensioned to allow passage of push/pull cable 8 and includes a pair of flat sidewalls 140. Second mounting block 132 also includes a threaded bore 142 dimensioned to receive a threaded stop 144. Threaded stop 144 can be selectively positioned within throughbore 112 to set the maximum stroke of drive member 128.

Push/pull cable 8 includes an outer sheath 146 and push/pull core 43. A rectangular fitting 147 is secured to one end of outer sheath 146. Fitting 147 is positioned between sidewalls 140 of mounting block 132 to fix outer sheath 146 relative to mounting block 132. Push/pull core 43 is slidably positioned within outer sheath 146. A second flag 148 is fastened to the end of push/pull core 43 opposite flag 42. As discussed above with respect to flag 42, flag 148 is formed from a piece of folded sheet metal which is crimped or fastened in some other manner to push/pull core 43. Second flag 148 includes a hub portion 150 and a pennant portion 152 having a tongue 154 which is dimensioned to be received within annular recess 130 of drive member 128.

Prior to operating the biopsy system, flag 148 and push/pull core 43 are secured within trocar driver 100 by positioning push/pull core 43 and hub portion 150 in recess 115 with pennant portion 152 of flag 148 extending through radially extending slot 114 and tongue 154 extending into annular recess 130 of drive member 128. Recess 115 is dimensioned to prevent buckling of push/pull core 43. To facilitate installation of flag 148 into trocar driver 100, each end of housing halves 110a and 110b include a stepped portion 156 adjacent each end of radially extending slot 114. Stepped portions 156 are in juxtaposed alignment when housing halves 110a and 110b are fastened together to provide an enlarged slot 158 to accommodate installation of hub portion 150 of flag 148 into recess 115.

Referring to FIGS. 13, 14 and 27–29, knife driver 200 includes a motor 210, a drive gear 212, a driven gear 214, a tri-roller bearing assembly 216, a return actuator 218, a forward bearing assembly 220, a limit switch assembly 222, and a baseplate 223. Motor 210 is preferably a DC servo motor or an AC motor. In the alternative, motor 210 can be any type of electrically, hydraulically or pneumatically driven motor. Motor 210 turns drive gear 212 which in turn drives driven gear 214. Driven gear 214 is connected to a cylindrical shaft 224 using a known fastening technique, e.g., crimping, welding, etc., such that upon rotation of driven gear 214, shaft 224 is rotatably driven. Shaft 224 is preferably a solid metal shaft, but may be hollow and formed of any material having the requisite strength requirements. Shaft 224 extends from driven gear 214 and extends through tri-roller bearing assembly 216 into outer sheath 225 of knife driver cable 6. Knife driver cable 6 includes outer sheath 225 and inner flexible shaft 226. Inner flexible shaft 226 preferably includes a solid core diameter with alternately wound layers about the solid core diameter. Alternately, different types of flexible shafts capable of accurately translating rotational and axial movement to the knife assembly of SULU 10 may be used. Shaft 224 is secured to flexible shaft 226 such as by welding, although other fastening techniques may be employed.

Figure 27:
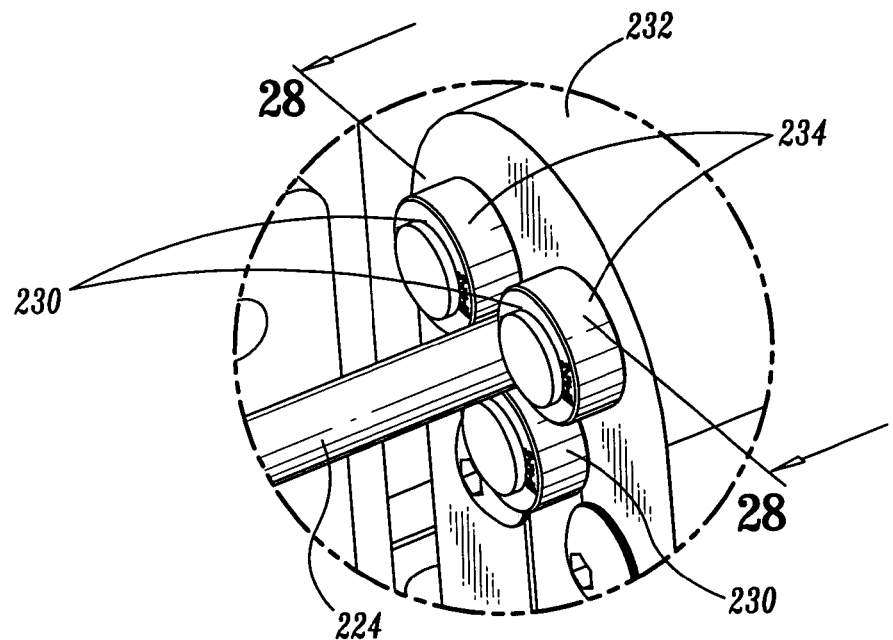
FIG. 27 is an enlarged view of the indicated area of detail of FIG. 13.
Figure 28:
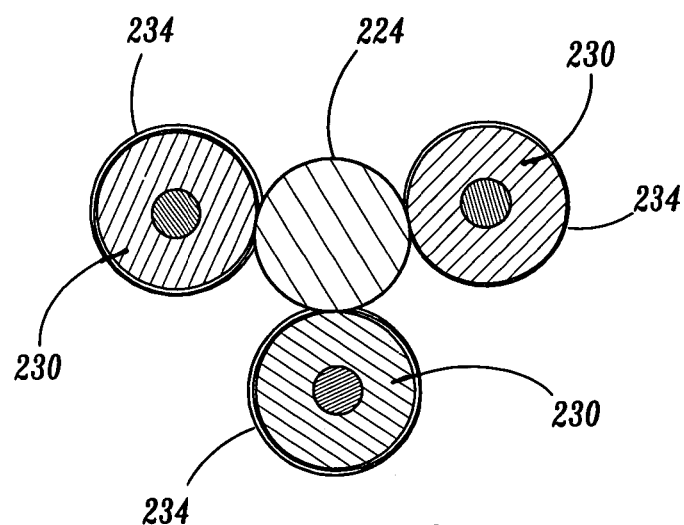
FIG. 28 is a cross-sectional view taken along section lines 28—28 in FIG. 27.
Figure 29:
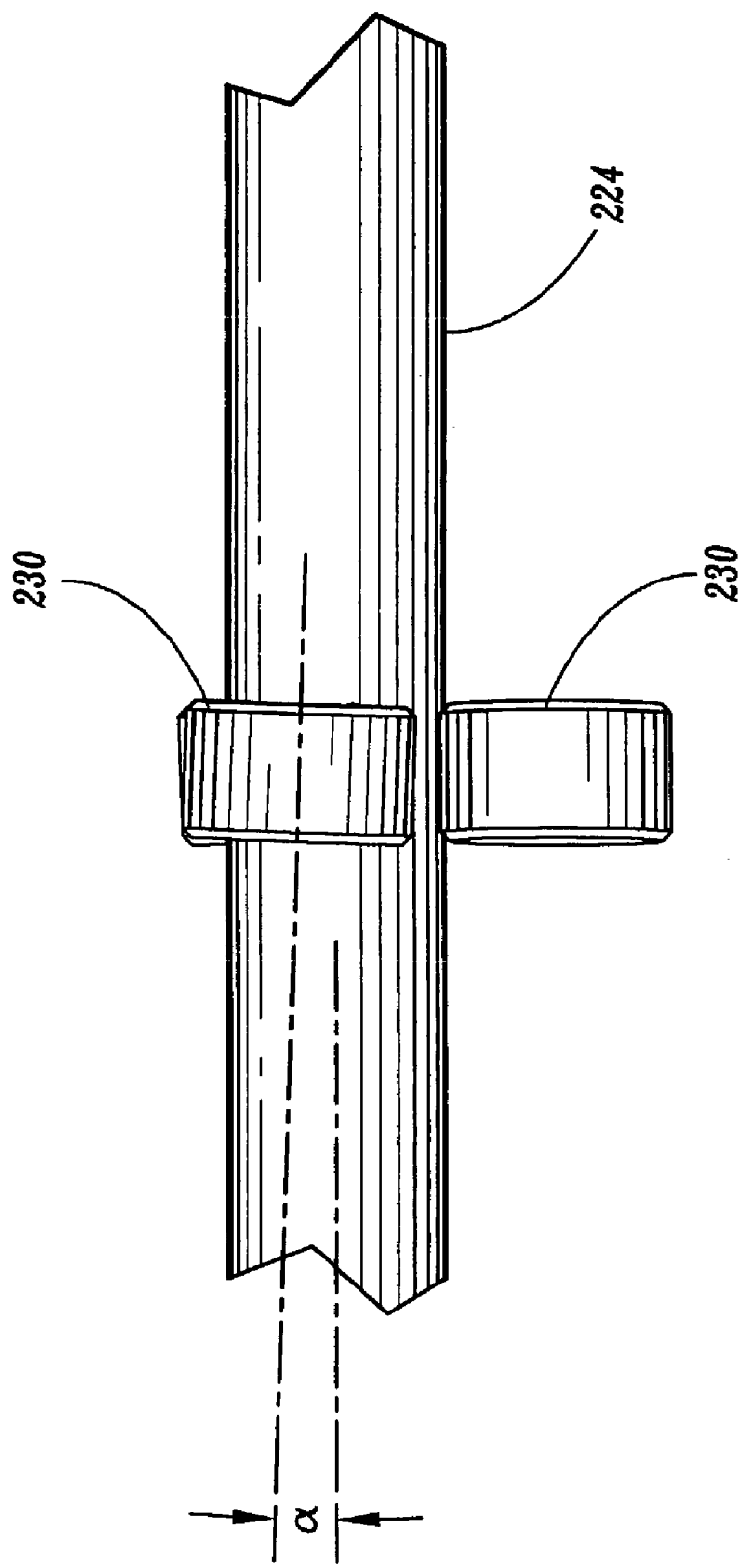
FIG. 29 is a side view of the tri-roller bearing assembly and shaft of the knife driver of FIG. 13.
Figure 34:
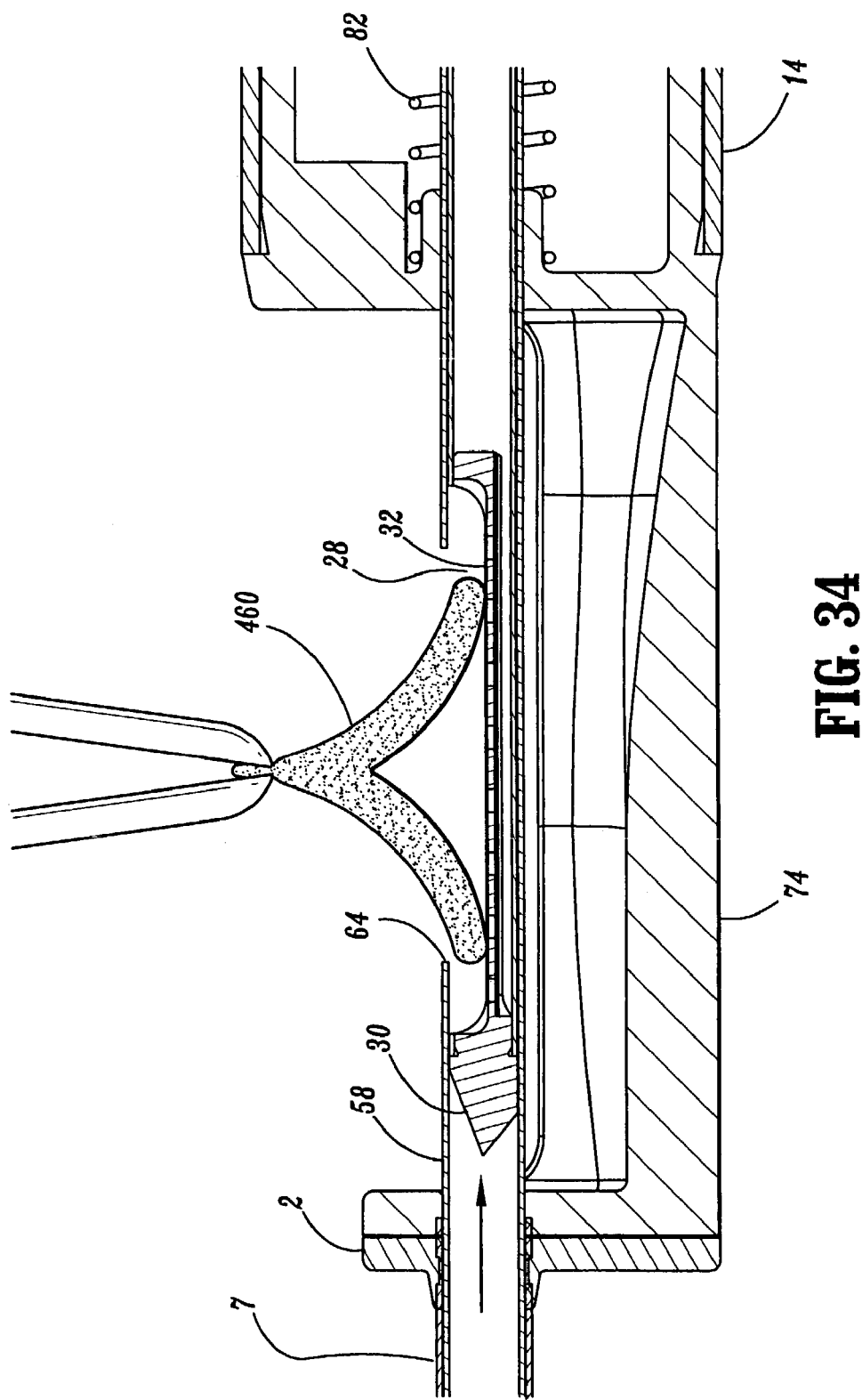
FIG. 34 is a side cross-sectional view of a central portion of the SULU with the trocar in the retracted position and the basket disposed adjacent the tissue access window, wherein a tissue sample is being removed from the window.

Referring specifically to FIGS. 27 and 28, tri-roller bearing assembly 216 includes three bearing elements 230 mounted on bearing support 232. Each of bearing elements 230 is oriented and configured to have contact surfaces 234 which form a partially helical thread configuration and effects axial translation of shaft 224 as shaft 224 is rotated by driven gear 214. Specifically, each of bearing elements 230 is tilted at an angle $\alpha$ which is offset from the longitudinal axis (FIG. 29). This angle of offset $\alpha$ may be chosen to achieve a desired rate of advancement per revolution of shaft 224. One effective angle for present purposes is approximately 2°, although other offset angles are envisioned.

Return actuator 218 includes a cylinder 238 and a piston 240. A follower 242 is connected to piston 240. Follower 242 includes a U-shaped recess 244 dimensioned to be positioned about shaft 224. As shaft 224 is rotated and advanced axially, follower 242 is pushed axially to extend piston 240 from within cylinder 238. When it is desired to return shaft 224 to its retracted position, a vacuum is effected within cylinder 238 to retract piston 240. When piston 240 is retracted, follower 242 urges disc 246 rearwardly to return shaft 224 to its retracted position. The return force applied to shaft 224 by return actuator 218 must be greater than the slip force applied on shaft 224 by tri-roller bearing assembly 216. Currently, the slip force applied on shaft 224 by tri-roller assembly 216 is approximately 2 lbs. and the return force applied by return actuator 218 is approximately 9 lbs.

A side bracket 250 is secured to baseplate 223. Limit switch assembly 222 is supported on side bracket 250 and includes a pair of limit switches 252 and 254. Limit switch 252 is positioned to engage disc 246 to release the vacuum from air cylinder 238 after piston 240 and shaft 224 have been moved to their retracted position. Limit switch 254 is positioned to engage disc 246 to shut down motor 210 when shaft 224 has reached the predetermined end of its stroke.

Typically, bearing elements 230 are spaced 120° apart. Alternately, as illustrated in FIG. 28, the spacing between the two uppermost bearing elements may be increased to allow shaft 224 to be snap fit in between the uppermost bearing elements 230. The lowermost bearing element is spring mounted on a slide 235 which is slidably positioned within an elongated vertical recess 232' formed in bearing support 232. A pair of screws 237 retain slide 235 slidably positioned within recess 232!. A spring (not shown) positioned in the bottom of slide 235, urges slide 235 and bearing 230 upwardly. By mounting one of the bearing elements 230 on a spring mounted slide, the tolerances normally required to achieve the desired slip force are no longer necessary and the desired slip force can be more easily attained.

Figure 19:
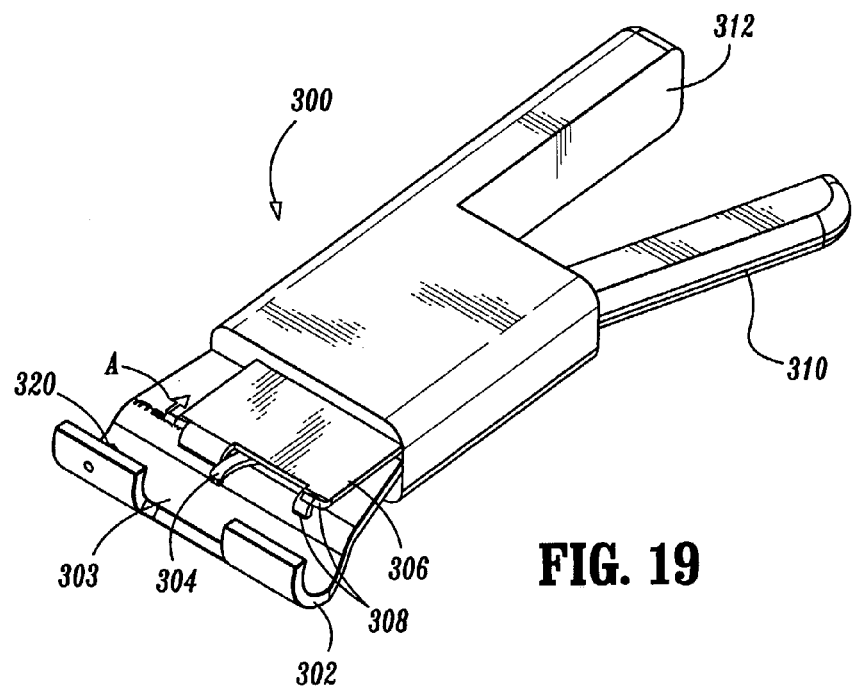
FIG. 19 is a perspective view of the firing module for use with the SULU shown in FIG. 2.
Figure 20:
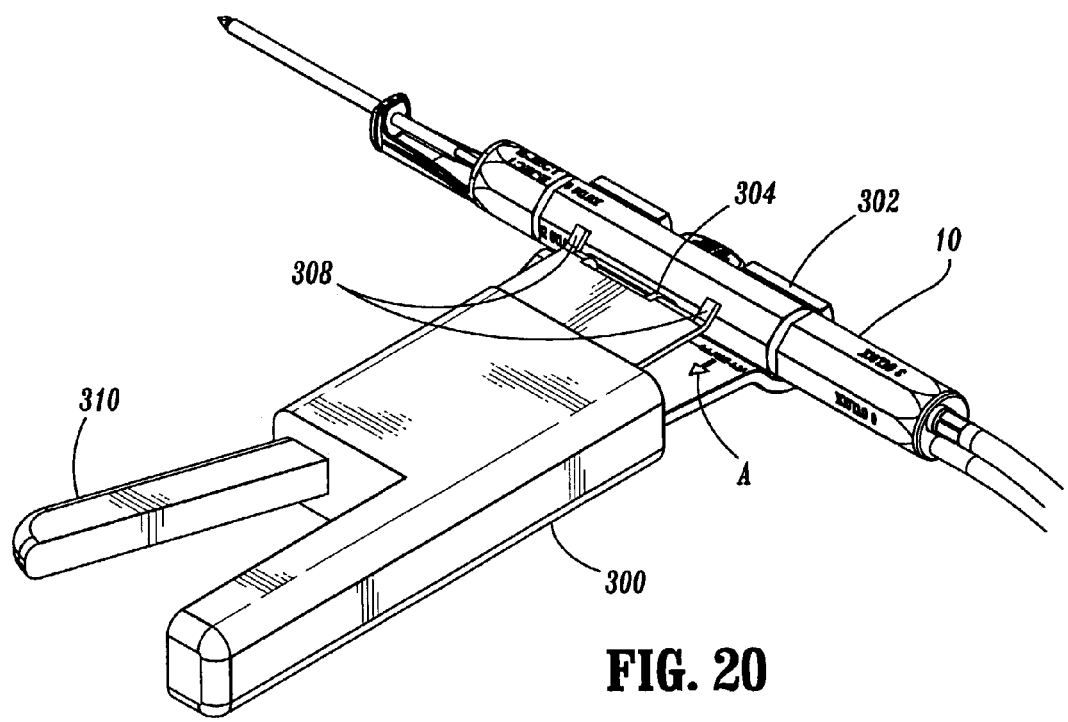
FIG. 20 is a perspective view of the SULU shown in FIG. 2 with the firing module shown in FIG. 19 attached thereto.

Referring to FIGS. 19 and 20, a firing module 300 is adapted to engage tubular body 14 of SULU 10 to effect firing of trocar 22 into tissue. Firing module 300 includes a support member 302, a firing lever 304, and a positioning bracket 306. Support member 302 defines a concavity 303 configured to receive SULU 10. Positioning bracket 306 includes a plurality of fingers 308 which engage and retain SULU 10 on support member 302 in concavity 303 when SULU 10 is supported thereon.

Firing module 300 includes a handle assembly including a movable handle 310 and a stationary handle 312. Movable handle 310 can be compressed towards stationary handle 312 to load firing lever 304. When movable handle 310 is moved towards stationary handle 312, support member 302 is moved away from positioning bracket 306 to allow SULU 10 to be positioned in concavity 303 of support member 302. When movable handle 310 is released, support member 302 moves in the direction indicated by arrow "A" to clamp SULU 10 between support member 302 and positioning bracket 306 such as shown in FIG. 20.

Figure 21:
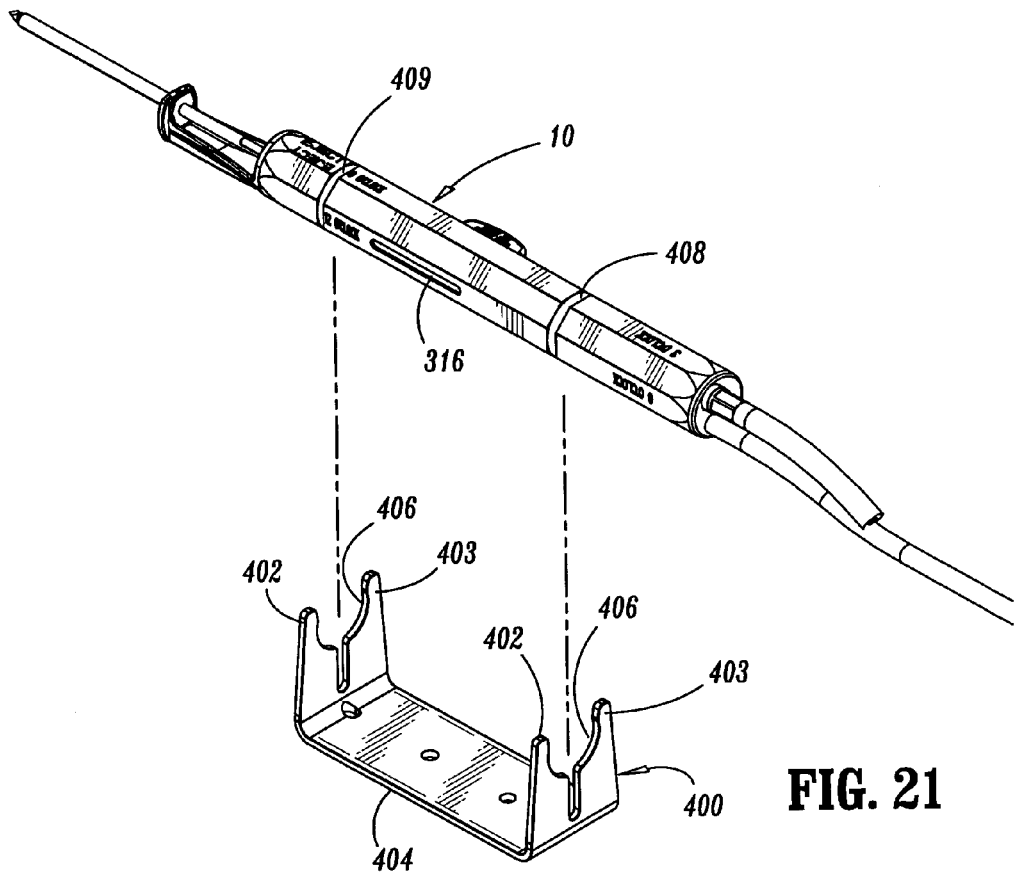
FIG. 21 is a perspective view of the SULU as shown in FIG. 2 positioned adjacent to a mounting cradle.

Referring also to FIG. 21, tubular body 14 of SULU 10 includes an elongated slot 316. When firing module 300 is attached to SULU 10, firing lever 304 extends through slot 316 to a position behind trocar flange 34 (see FIG. 4). A release pin 320 is positioned on support member 302. Release pin 320 is positioned to extend through opening 322 formed in tubular body 14 (FIG. 2) and engage a pin 324 formed on C-tube 46. Engagement between release pin 320 and pin 324 causes C-tube 46 to rotate slightly, moving notch 56 out of engagement with trocar flange 34. By disengaging flag 42 from trocar flange prior to firing, the drag on the firing module is greatly reduced, allowing trocar 22 and trocar tip 30 to be accelerated more quickly and thus, advanced at a greater velocity into a targeted tissue mass.

Figure 22:
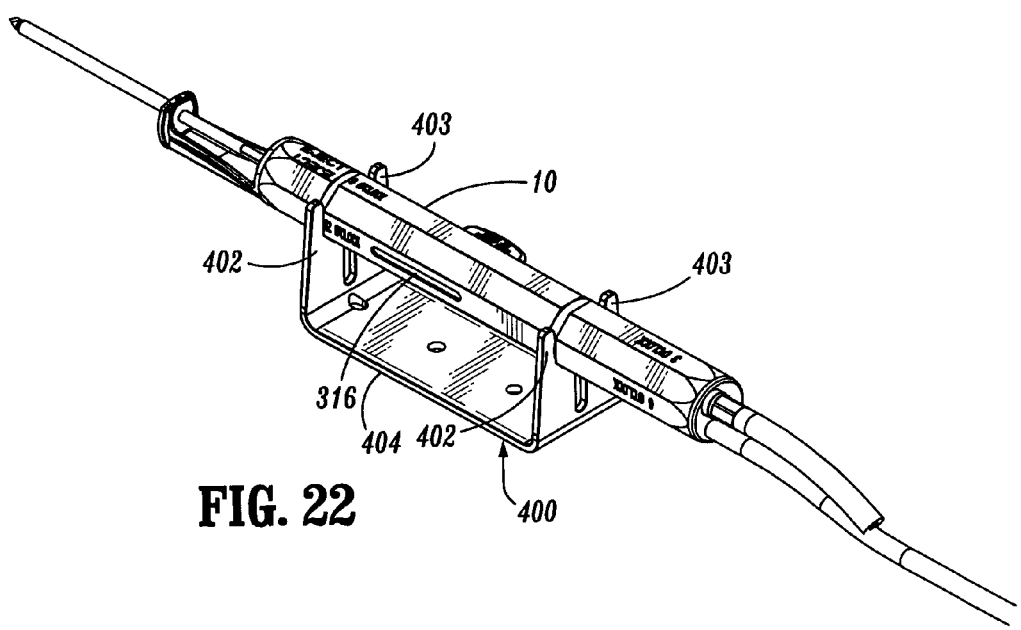
FIG. 22 is a perspective view of the SULU shown in FIG. 2 supported on the mounting cradle.

Referring to FIGS. 21 and 22, SULU 10 can be hand held during operation, or in the alternative, SULU 10 can be supported on the instrument stage of a stereotactic imaging table. When SULU 10 is supported on an instrument stage, SULU 10 is first supported on a cradle 400. Cradle 400 includes a pair of spaced resilient arms 402 and 403 positioned at each end of a base member 404. Each pair of spaced arms defines a concavity 406 for receiving one end of SULU 10. Tubular body 14 of SULU 10 includes a pair of annular grooves 408 and 409. Arms 402 and 403 are dimensioned to be received within grooves 408 and 409 to axially fix SULU 10 in relation to cradle 400.

Figure 23:
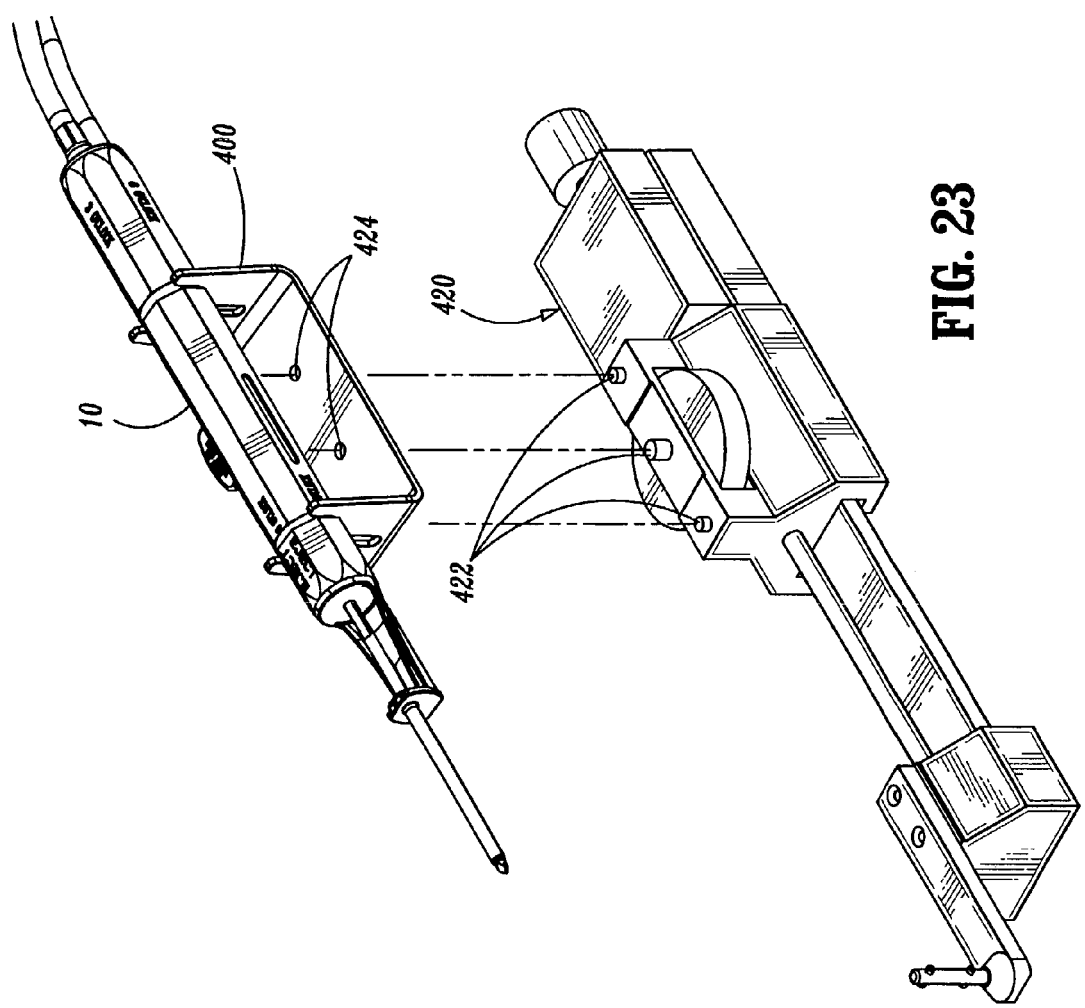
FIG. 23 is a perspective view of the SULU/cradle assembly shown in FIG. 22 positioned adjacent a table mount.
Figure 24:
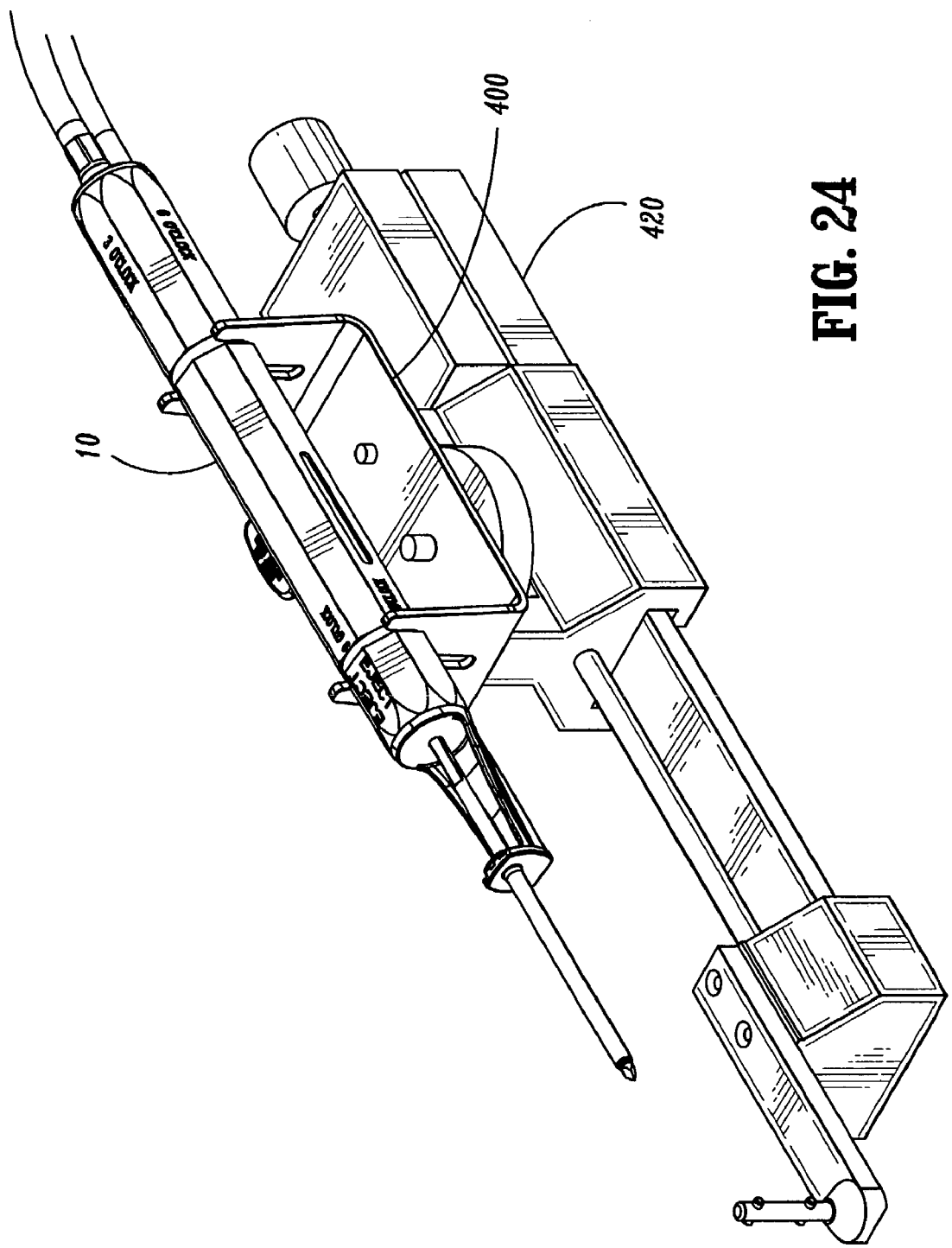
FIG. 24 is a perspective view of the SULU/cradle assembly shown in FIG. 24 positioned on a table mount.
Figure 25:
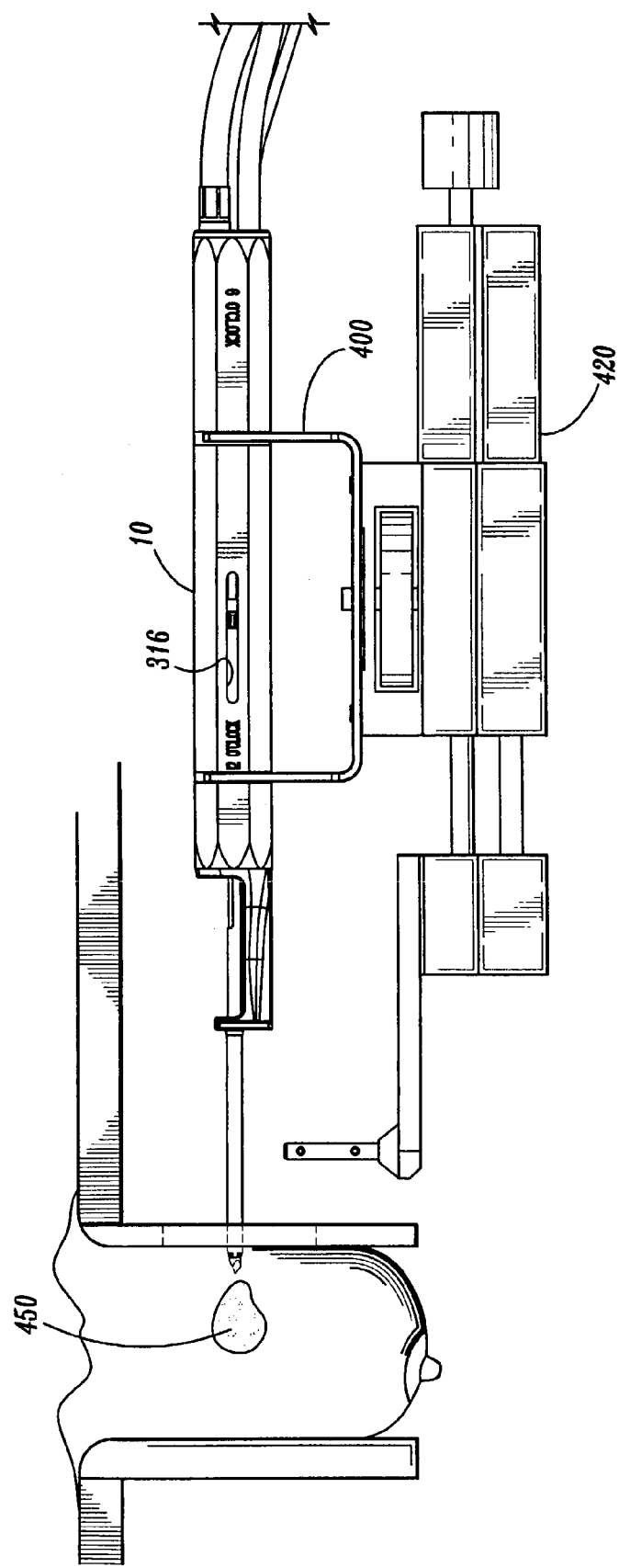
FIG. 25 is a side view illustrating the relative alignment of the SULU with a target tissue in a clamped breast prior to insertion of the trocar tip.
Figure 26:
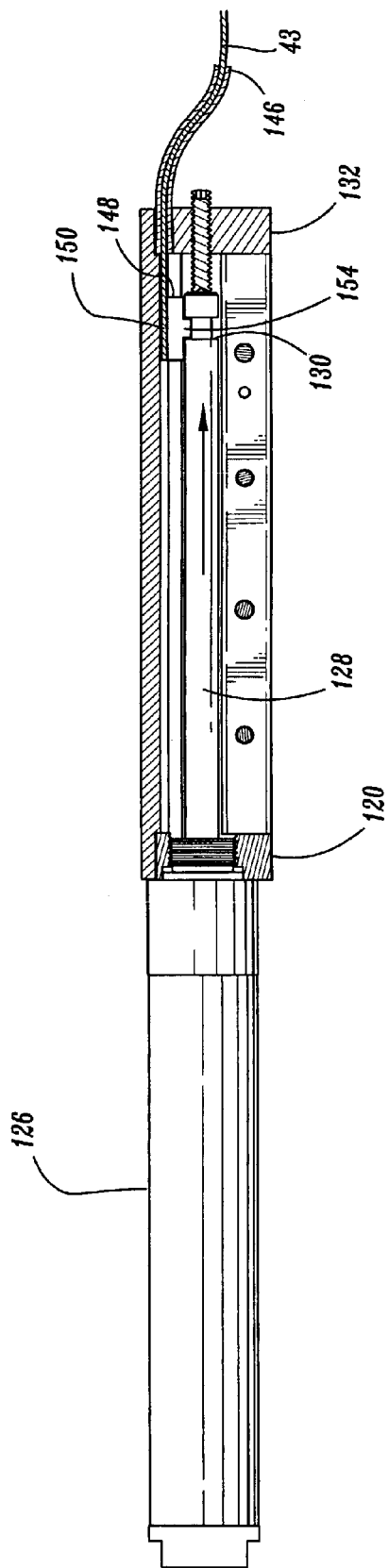
FIG. 26 is a side cross-sectional view of the trocar driver shown in FIG. 15 in the advanced position.

Referring to FIGS. 23 and 24, when SULU 10 is used in conjunction with an imaging table, cradle 400 is secured to stage or table mount 420. Typically, table mount 420 includes a plurality of protrusions 422 which are dimensioned to be received in holes 424 formed in cradle 400. Protrusions 422 on table mount 420 and holes 424 in cradle 400 are located to properly position SULU 10 on the imaging table.

Referring to FIGS. 25, 26 and 30–35, the operation of the biopsy system will now be described for use in connection with a biopsy procedure performed on a breast of a patient. It is to be understood, however, that the procedures described herein may also be utilized in connection with the biopsy of tissue in other regions of the body.

As discussed above, SULU 10 can be hand-held during use or supported on an imaging table. The following description is directed to use of the biopsy system after it has been positioned on an imaging table.

First, cradle 400 is secured to table mount 420. Next, shipping tab 79 is removed from slot 316 of SULU 10 and firing module 300 is clamped to SULU 10 in the manner discussed above such that firing lever 304 extends through opening 316 of tubular body 14 and engages the rear end of trocar flange 34. Attachment of firing module 300 to SULU 10 also effects rotation of C-tube 46 to disengage notch 56 of flag 42 from trocar flange 34. As discussed above, by disengaging flag 42 from trocar flange 34, drag on the firing module 300 is reduced and trocar 22 can be accelerated more quickly to a higher velocity prior to engaging the targeted tissue mass 450.

After SULU 10 has been secured within cradle 400 on table mount 420, SULU 10 is moved using table mount 420 in association with a stereotactic imaging apparatus to a position in which trocar tip 30 is aligned with the center of a targeted tissue mass 450. With trocar 22 and tubular knife 58 in a retracted position, trocar tip 30 is targeted, i.e., advanced to a position approximately 17 mm in front of targeted tissue mass 450. See FIG. 25.

Next, a release button (not shown) on firing module 300 is actuated to release firing lever 304 to advance trocar flange 34 and trocar 22 into targeted tissue mass 450. See FIG. 32. In this position trocar 22 is in the advanced position with receiving basket 28 positioned within targeted tissue mass 450, and knife 58 is in the retracted position.

At this point, a vacuum is drawn through vacuum tube 95, trocar 22 and basket insert 32 via vacuum line 12 (FIG. 3) to draw tissue into basket 28. After tissue has been drawn into basket 28, knife driver can be actuated to advance knife 58 over trocar 22 (FIG. 33). As discussed above, knife driver 200 advances and rotates knife 58 to sever the tissue positioned in basket 28 from the targeted tissue mass. After knife 58 has been moved to the advanced position, a tissue sample 460 cut from targeted tissue mass 450 is positioned within basket 28. See FIG. 33.

Figure 35:
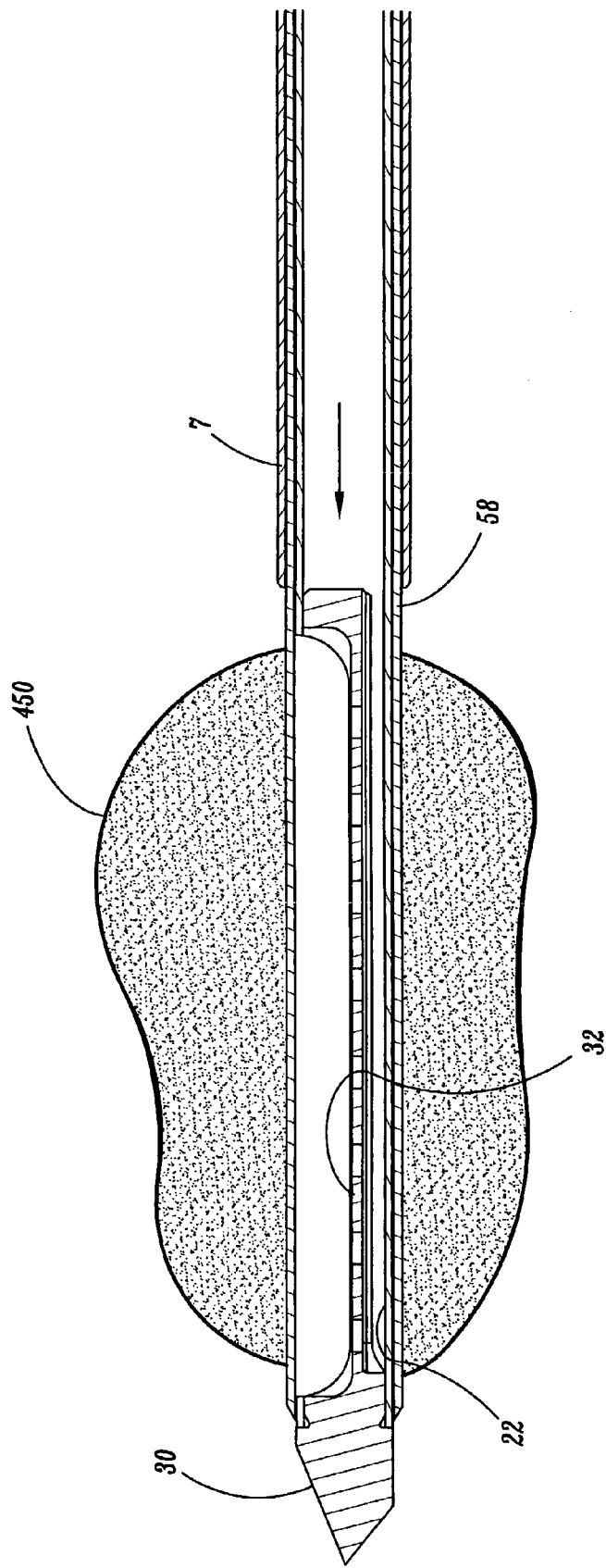
FIG. 35 is a side cross-sectional view of the distal end of the SULU disposed within a target tissue mass with the knife assembly and the trocar assembly in the advanced position.

In order to retrieve sample 460 from basket 28, firing module 300 is first disengaged from SULU 10 by cocking or compressing the movable handle of firing module 300 to allow C-tube 46 to be returned by spring 55 to a position in which notch 56 of flag 42 is positioned to engage trocar flange 34. Thereafter, trocar driver 100 is actuated to advance push/pull core 43 and flag 42 into engagement with trocar flange 34. Due to the configuration of flag 42 and trocar flange 34, notch 56 of flag 44 will be cammed into engagement with trocar flange 34 as push/pull core 43 is advanced. After flag 42 engages trocar flange 34, needle driver 100 is actuated to move push/pull core 43, trocar flange 34 and trocar 22 to a retracted position wherein basket 28 is positioned below window 64 formed in knife 58. Tissue sample 460 can now be removed from basket 28 through window 64. It is noted that in this position, knife 58 remains at a fixed position within target tissue mass 450. Thus, if additional tissue samples are desired, trocar driver 100 need only be actuated to move trocar 22 back to the advanced position. See FIG. 35. At this point, knife 58 can be retracted to expose basket 28 to target tissue mass 450. Thereafter, a vacuum can be drawn through vacuum tube 95 to draw another tissue sample into basket 28 and knife 58 can be advanced to sever the tissue sample from tissue mass 450. If it is desired to obtain a tissue sample from a different portion of targeted tissue mass 450, the entire SULU 10 can be rotated to rotate basket 28 to any particular orientation with respect to tissue mass 450 to obtain a tissue sample from a particular location within tissue mass 450. For example, SULU 10 can be rotated 180 to obtain a second tissue sample from an opposite side of tissue mass 450. Alternately, SULU 10 can be rotated 30, 60, 90, 120 etc. Indicia 20 on tubular body 14 identifies the particular orientation of SULU 10. It is noted that SULU is preferably rotated when trocar 22 and knife 58 are in the advanced position as shown in FIG. 35.

When SULU 10 is hand-held during operation, firing module 300 is not required. Rather, with the aid of X-ray, the trocar tip is manually advanced through the targeted tissue mass such that basket 28 spans the entire width of target tissue mass 450. Thereafter, the procedure is identical to that disclosed above with respect to operation of the biopsy system when SULU 10 is mounted on table mount 420.

Figure 36:
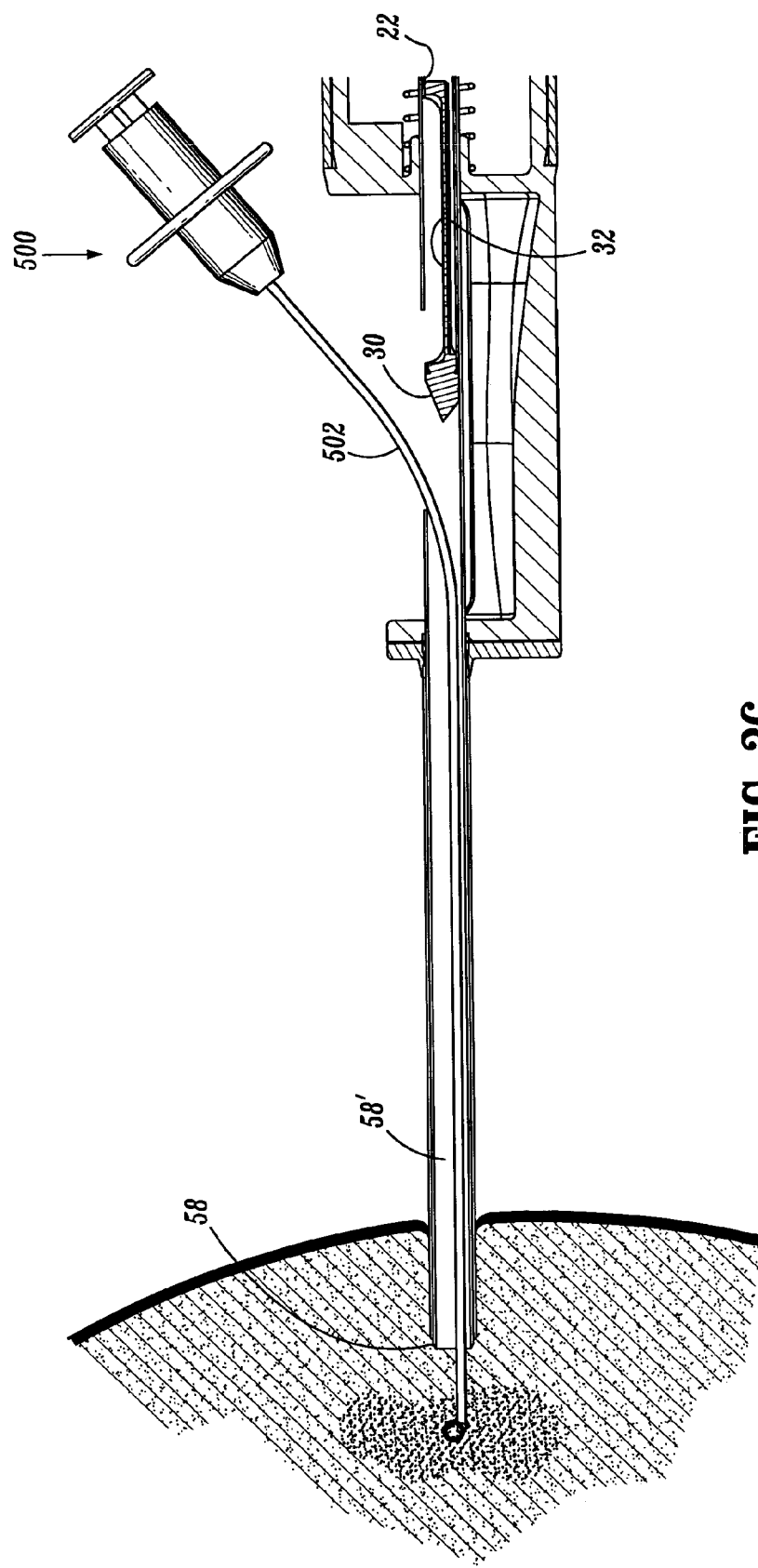
FIG. 36 is a side cross-sectional view of the forward and of the SULU disposed within a target tissue mass with the trocar assembly in a retracted position and a tissue marking device extending through the tubular knife.

Referring to FIG. 36, trocar 22 can be retracted to a position proximal of window 64 to provide access to an internal channel 58' of tubular knife 58. Surgical instrumentation may be inserted through internal channel 58' prior to and/or after the biopsy procedure as needed. For example, the flexible delivery tube 502 of a site marker device 500 can be passed through knife 58 to position a hoop marker at the biopsy site. Such a site marker device is disclosed in PCT/US99/24867 filed Oct. 22, 1999 and U.S. provisional application No. 60/105,419, filed Oct. 23, 1998, both of which are incorporated herein by reference in their entirety.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A biopsy system which comprises:
   a loading unit which includes a trocar defining a tissue receiving basket, and a knife;
   a trocar driver operatively associated with the trocar between an engaged configuration and a disengaged configuration such that the trocar and the trocar driver may move independent of one another, the trocar driver being actuable to move the trocar between advanced and retracted positions;
   a knife driver operatively associated with the knife and being actuable to move the knife between retracted and advanced positions; and
   a firing module operatively associated with the trocar and adapted to advance the trocar into a targeted tissue mass when the trocar driver and the trocar are configured in the disengaged configuration.

2. A biopsy system according to claim 1, wherein the firing module is removably attached to the loading unit.

3. A biopsy system according to claim 1, which further comprises a connecting member which operably connects the trocar driver and the trocar.

4. A biopsy system according to claim 3, which further comprises a trocar flange connected to the trocar, the trocar flange being positioned to be driven by the firing module to advance the trocar into tissue.

5. A biopsy system according to claim 4, wherein the connecting member is movable from a first position in engagement with the trocar to a second position in disengagement with the trocar.

6. A biopsy system according to claim 5, wherein the connecting member includes a flag member at one end which is connected to the trocar driver.

7. A biopsy system according to claim 5, wherein the connecting member includes a flag member at one end which is adapted for engagement with the trocar flange.

* * * * *